(12) United States Patent
Kim et al.

(10) Patent No.: US 10,478,082 B2
(45) Date of Patent: Nov. 19, 2019

(54) FILM-TYPE BIOMEDICAL SIGNAL MEASURING APPARATUS, BLOOD PRESSURE MEASURING APPARATUS USING THE SAME, CARDIOPULMONARY FITNESS ESTIMATING APPARATUS, AND PERSONAL AUTHENTICATION APPARATUS

(71) Applicant: SEOUL NATIONAL UNIVERSITY R&DB FOUNDATION, Seoul (KR)

(72) Inventors: Hee Chan Kim, Seoul (KR); Seung Woo Noh, Busan (KR); Chi Yul Yoon, Seoul (KR)

(73) Assignee: Seoul National University R&DB FOUNDATION, Seoul (KR)

( * ) Notice: Subject to any disclaimer, the term of this patent is extended or adjusted under 35 U.S.C. 154(b) by 1091 days.

(21) Appl. No.: 14/779,570

(22) PCT Filed: Mar. 24, 2014

(86) PCT No.: PCT/KR2014/002469
§ 371 (c)(1),
(2) Date: Sep. 24, 2015

(87) PCT Pub. No.: WO2014/157896
PCT Pub. Date: Oct. 2, 2014

(65) Prior Publication Data
US 2016/0051156 A1    Feb. 25, 2016

(30) Foreign Application Priority Data

Mar. 24, 2013 (KR) .................. 10-2013-0031220
Jan. 23, 2014 (KR) .................. 10-2014-0008619
(Continued)

(51) Int. Cl.
*A61B 5/04* (2006.01)
*A61B 5/0408* (2006.01)
(Continued)

(52) U.S. Cl.
CPC .......... *A61B 5/04085* (2013.01); *A61B 5/021* (2013.01); *A61B 5/0205* (2013.01);
(Continued)

(58) Field of Classification Search
CPC . A61B 5/0402; A61B 5/0408; A61B 5/04085; A61B 5/04087; A61B 5/6801;
(Continued)

(56) References Cited

U.S. PATENT DOCUMENTS

2003/0115966 A1    6/2003  Ueno et al.
2004/0039419 A1*   2/2004  Stickney ................ A61B 5/046
                                                         607/5
(Continued)

FOREIGN PATENT DOCUMENTS

JP    2003-284697 A    10/2003
JP    3694740 B2        9/2005
(Continued)

OTHER PUBLICATIONS

International Search Report for PCT/KR2014/002469 dated Jul. 25, 2014 from Korean Intellectual Property Office.

*Primary Examiner* — Eun Hwa Kim
(74) *Attorney, Agent, or Firm* — Park, Kim & Suh, LLC

(57) ABSTRACT

Provided is a film-type biomedical signal measuring apparatus configured in a such a way that a plurality of metallic thin film electrodes and a circuit unit are formed on a film-type piezoelectric element so as to easily attach the apparatus to the skin and an electrical signal as well as an electrical signal of a human body is simultaneously measured using the plurality of metallic thin film electrodes and the circuit unit. Accordingly, the film-type biomedical signal measuring apparatus simultaneously measures electrocardiogram (ECG) and ballistocardiogram (BCG) from the simultaneously measured electrical signal and vibration sig-
(Continued)

nal of the human body and extracts biomedical information of various types of health indexes such as a heart rate, a stress index, BCG, a blood pressure, an amount of physical activity, a respiration rate, and VO$_2$max from the two different biomedical signals.

10 Claims, 13 Drawing Sheets

(30) Foreign Application Priority Data

Feb. 27, 2014 (KR) .................. 10-2014-0023359
Mar. 24, 2014 (KR) .................. 10-2014-0033957

(51) Int. Cl.
| | | |
|---|---|---|
| *A61B 5/021* | (2006.01) | |
| *A61B 5/11* | (2006.01) | |
| *A61B 5/0205* | (2006.01) | |
| *A61B 5/0432* | (2006.01) | |
| *A61B 5/117* | (2016.01) | |
| *A61B 5/00* | (2006.01) | |
| *A61B 5/024* | (2006.01) | |
| *A61B 5/08* | (2006.01) | |
| *A61B 5/0456* | (2006.01) | |

(52) U.S. Cl.
CPC ........ *A61B 5/02133* (2013.01); *A61B 5/0408* (2013.01); *A61B 5/0432* (2013.01); *A61B 5/04087* (2013.01); *A61B 5/1102* (2013.01); *A61B 5/117* (2013.01); *A61B 5/4866* (2013.01); *A61B 5/02438* (2013.01); *A61B 5/0456* (2013.01); *A61B 5/0816* (2013.01); *A61B 5/1118* (2013.01); *A61B 5/7278* (2013.01); *A61B 2562/0219* (2013.01); *A61B 2562/164* (2013.01)

(58) Field of Classification Search
CPC ............... A61B 5/6832; A61B 5/6833; A61B 2562/164; A61B 2562/02; A61B 2562/0204; A61B 5/02133; A61B 5/02438; A61B 5/117; A61B 5/0205; A61B 5/4866; A61B 5/0432; A61B 5/1102; A61B 5/1118; A61B 5/021; A61B 5/0456; A61B 5/7278
See application file for complete search history.

(56) References Cited

U.S. PATENT DOCUMENTS

| | | | |
|---|---|---|---|
| 2006/0030781 A1* | 2/2006 | Shennib | A61B 5/0402 600/509 |
| 2009/0076345 A1 | 3/2009 | Manicka et al. | |
| 2014/0039330 A1 | 2/2014 | Seo et al. | |
| 2014/0142451 A1 | 5/2014 | Kim et al. | |

FOREIGN PATENT DOCUMENTS

| | | | |
|---|---|---|---|
| JP | 2012-176106 | A | 9/2012 |
| KR | 10-2010-0128086 | A | 12/2010 |
| KR | 10-2012-0132732 | A | 12/2012 |
| KR | 10-1316497 | B1 | 10/2013 |
| KR | 10-1369754 | B1 | 3/2014 |

* cited by examiner

【FIG 1】
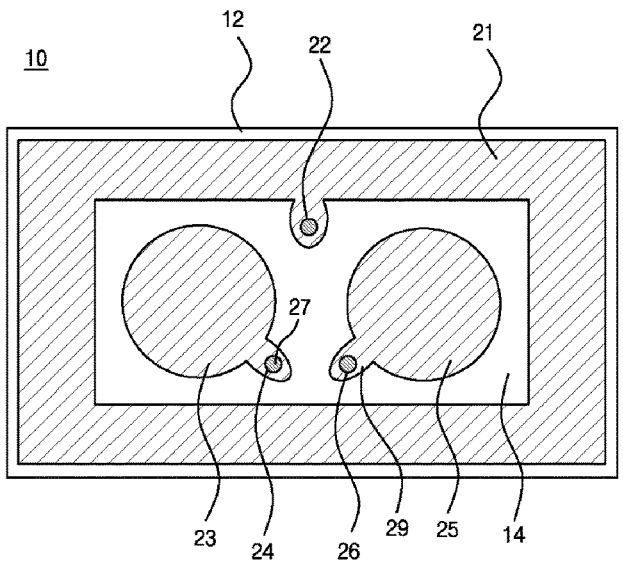
【FIG 2】
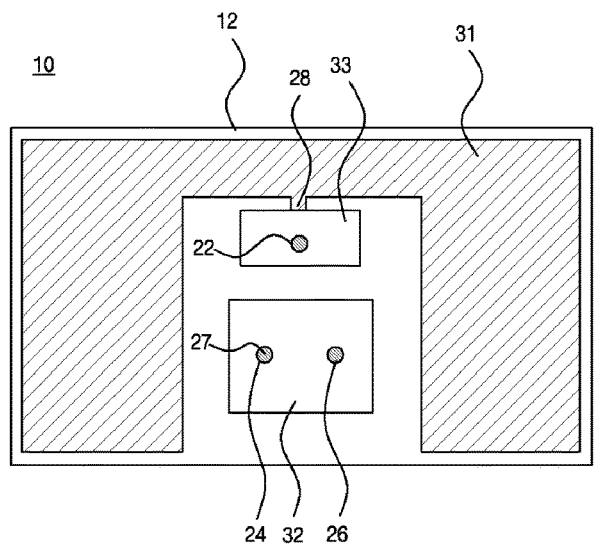
【FIG 3】
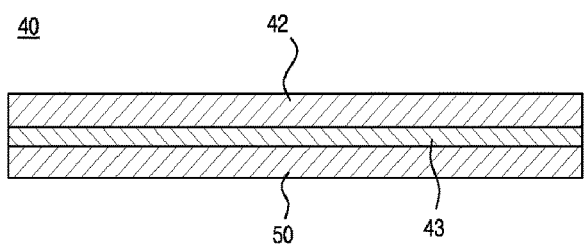

[FIG 4]
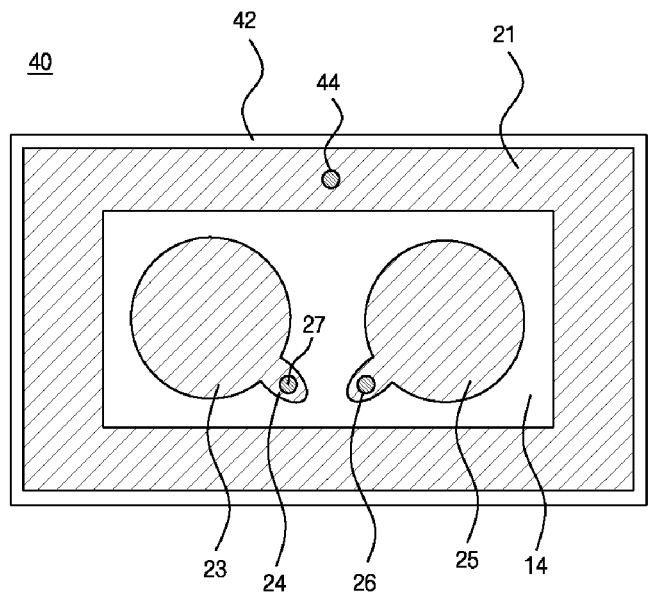
[FIG 5]
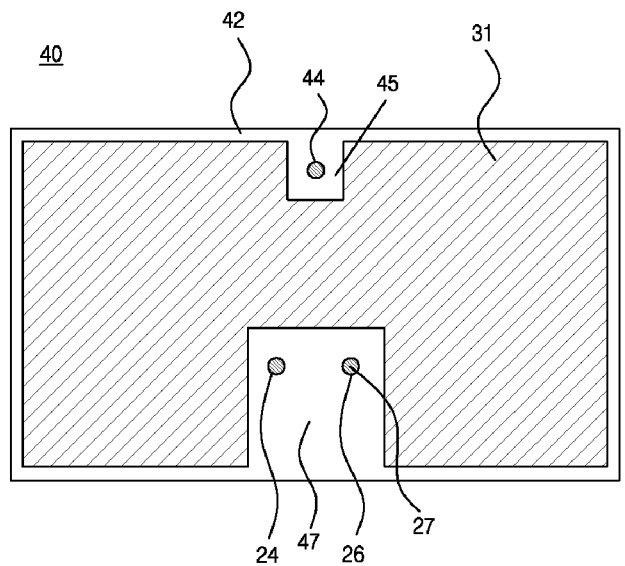

[FIG 6]
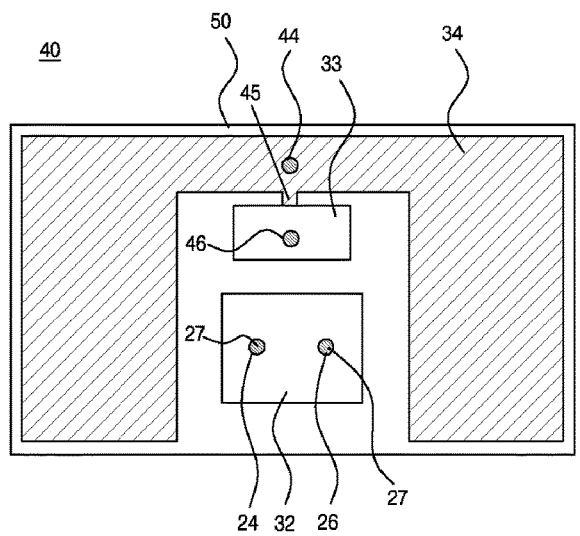
[FIG 7]
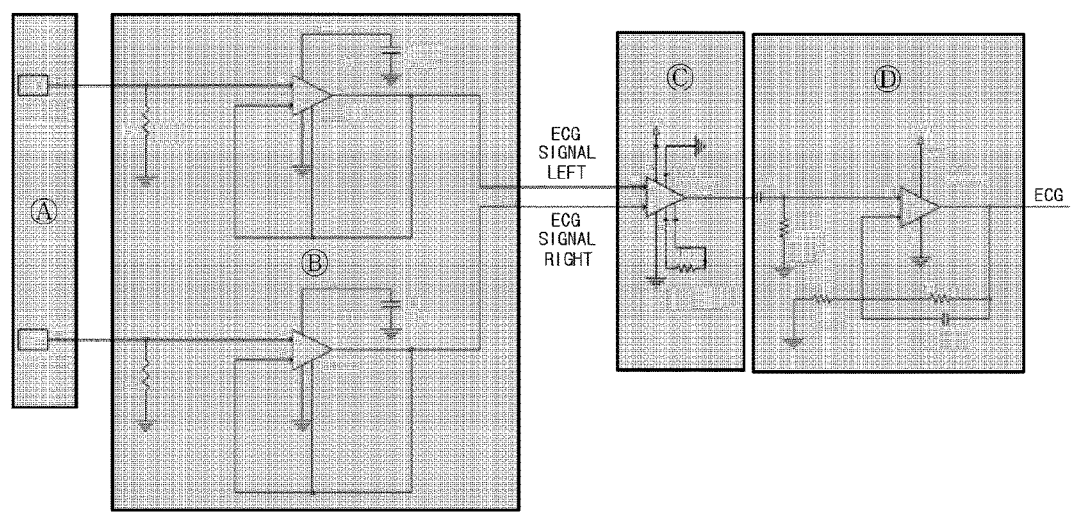

[FIG 8]
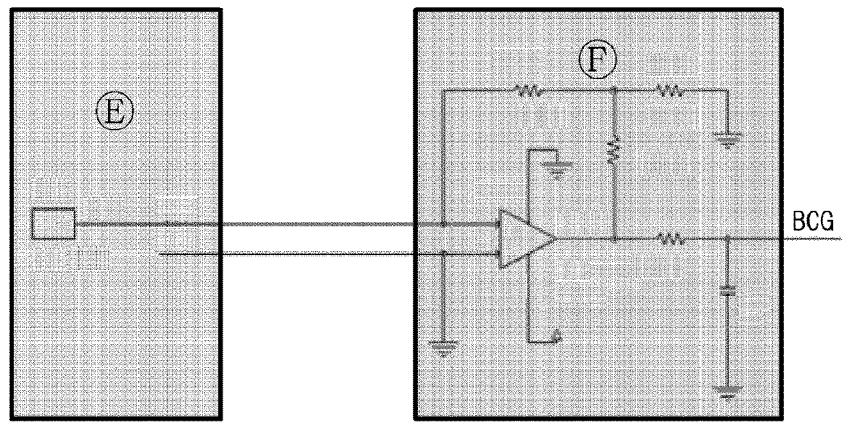
[FIG 9]
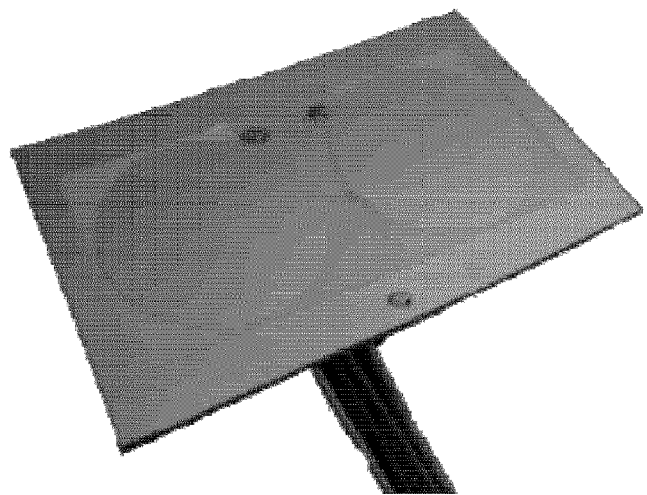
[FIG 10]
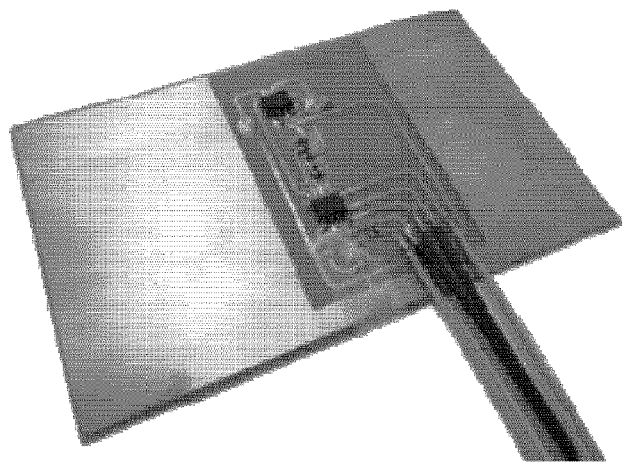

[FIG 11]
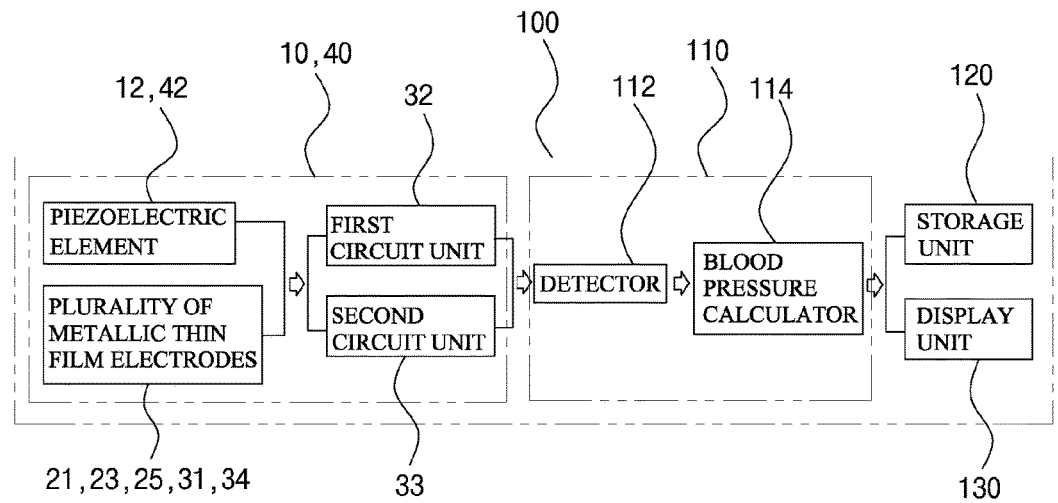
[FIG 12]
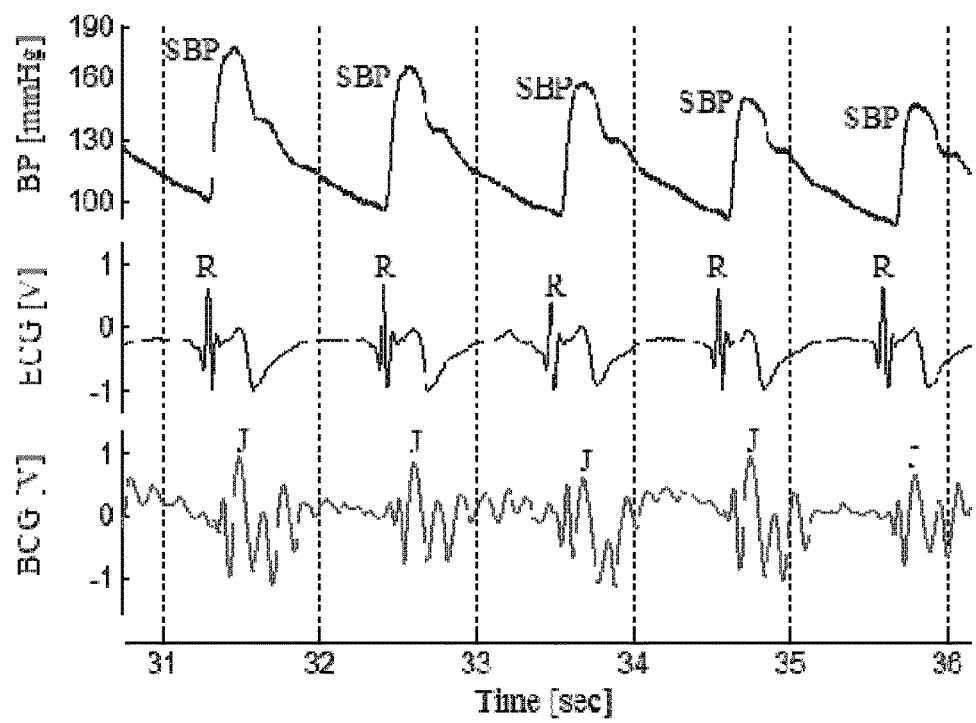

【FIG 13】
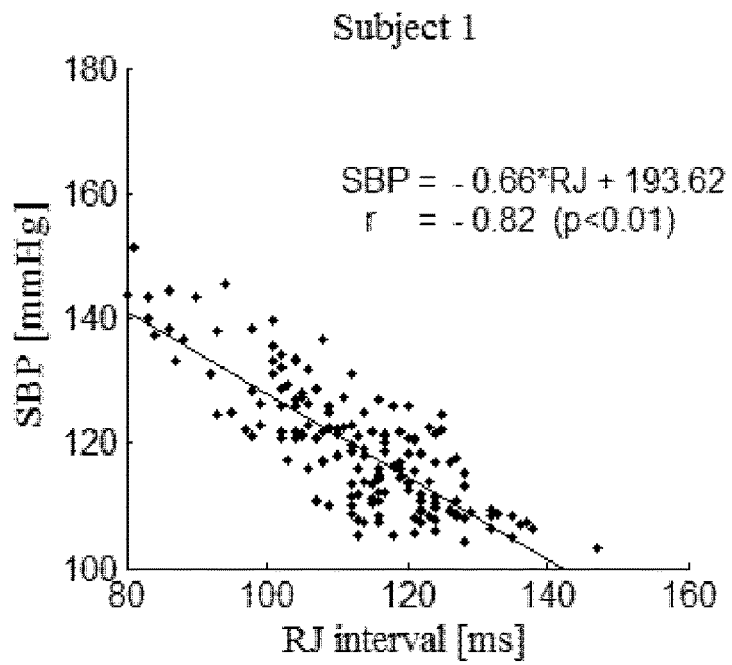
【FIG 14】
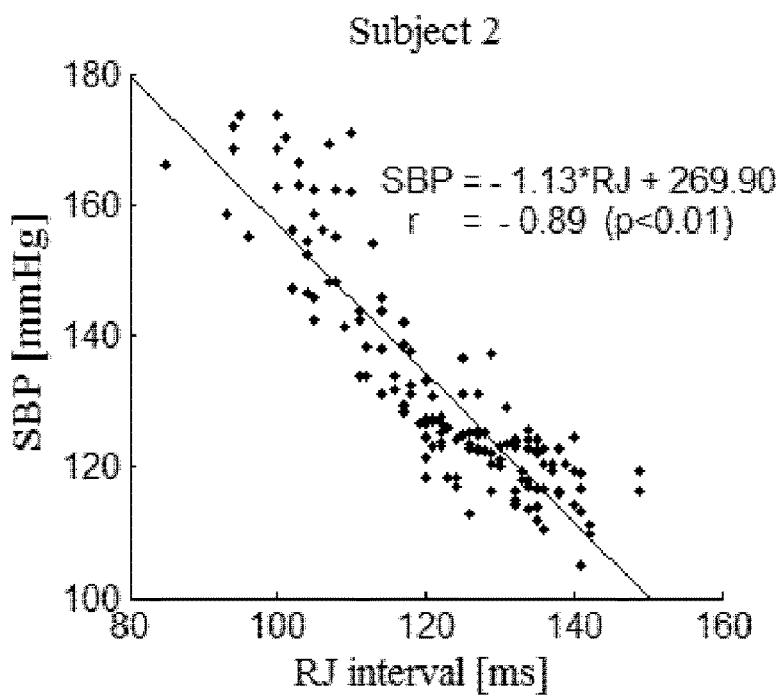

[FIG 15]
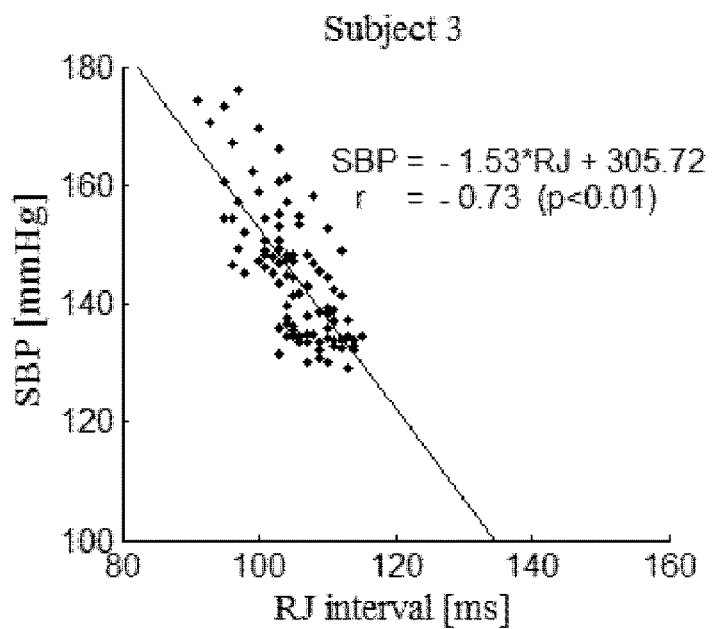
[FIG 16]
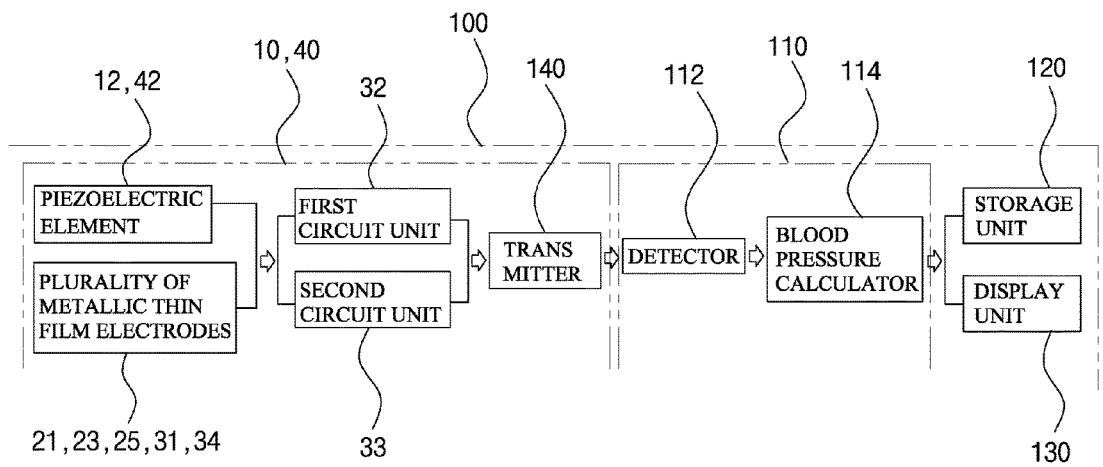

[FIG 17]
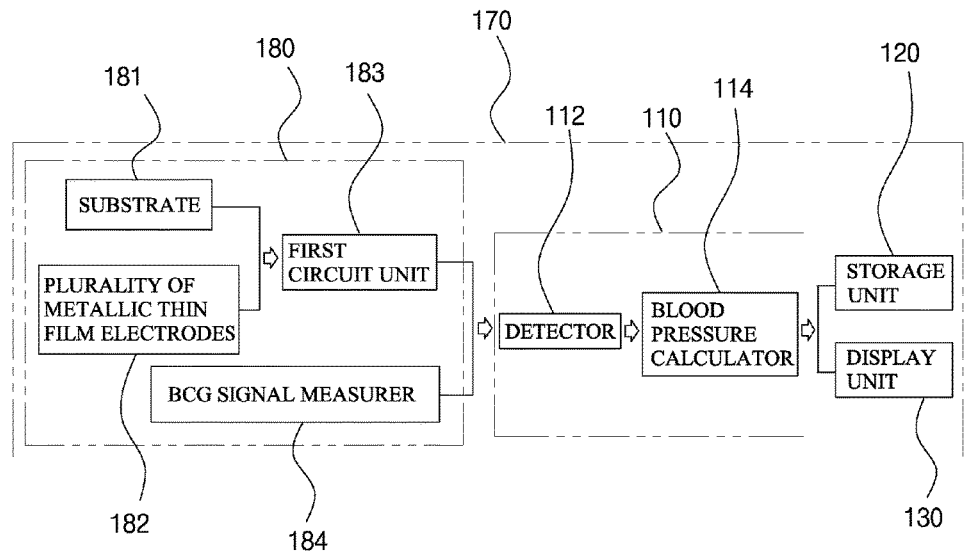
[FIG 18]
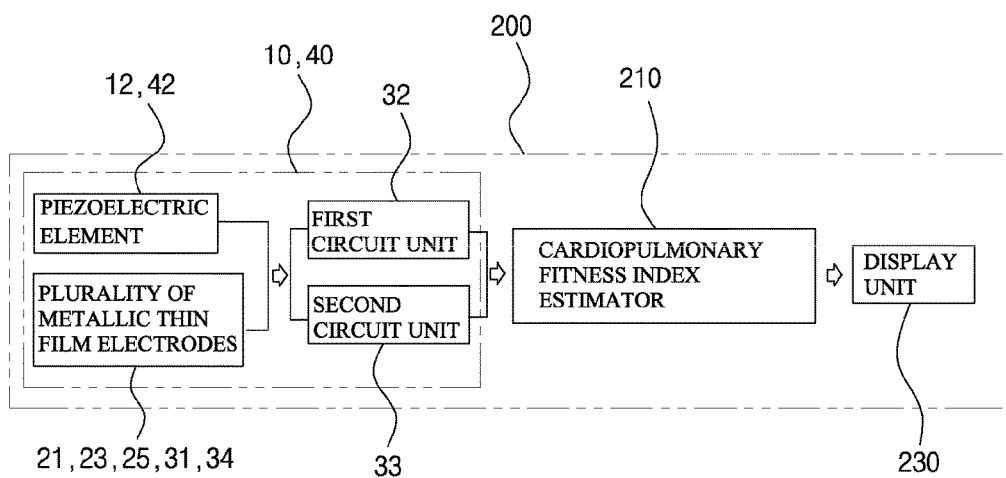

[FIG 19]
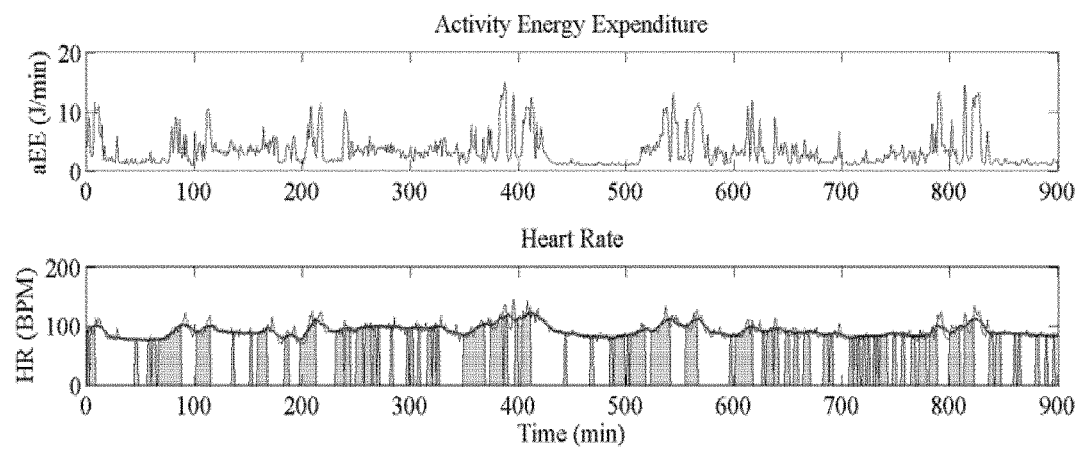
[FIG 20]
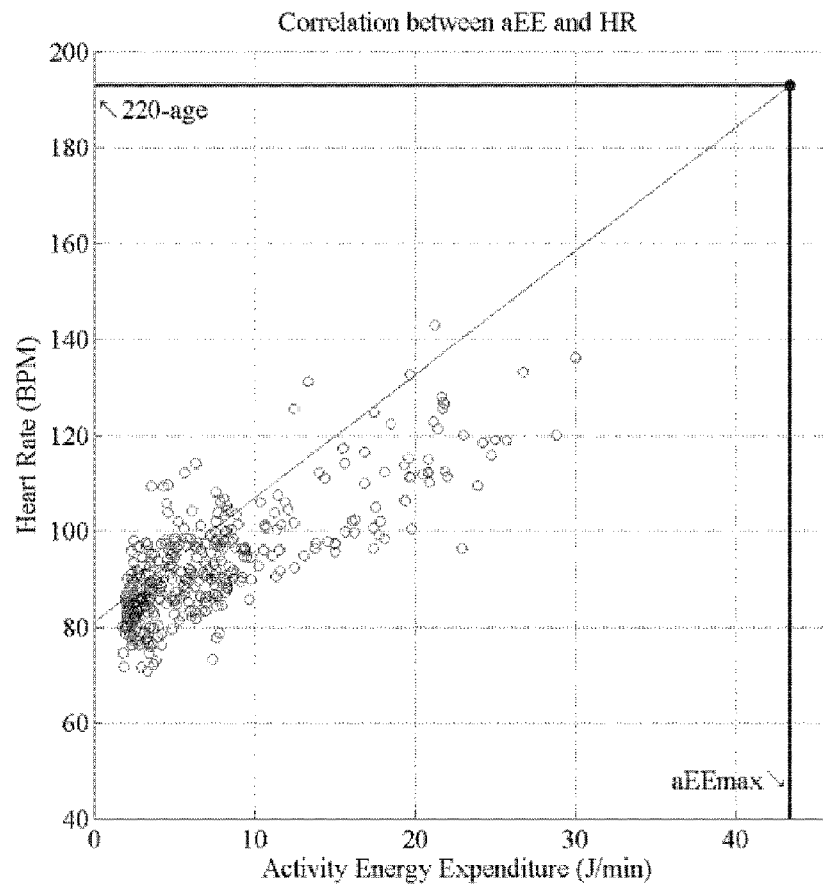

[FIG 21]
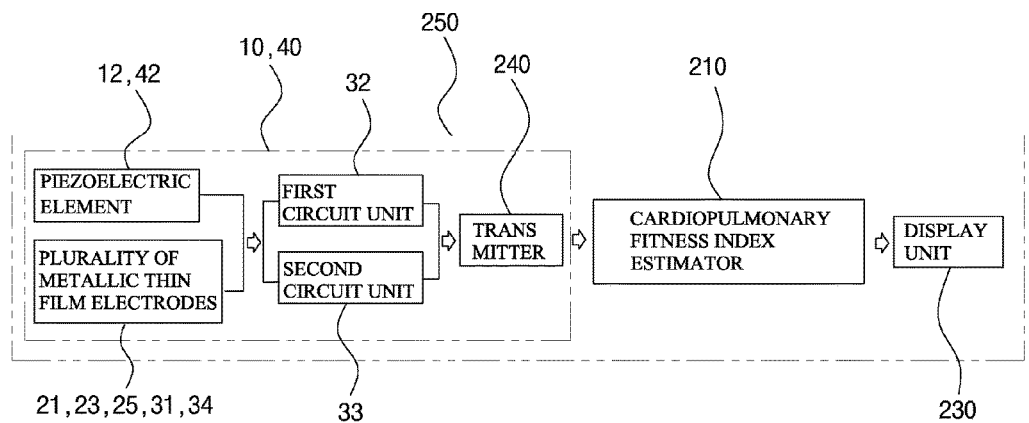
[FIG 22]
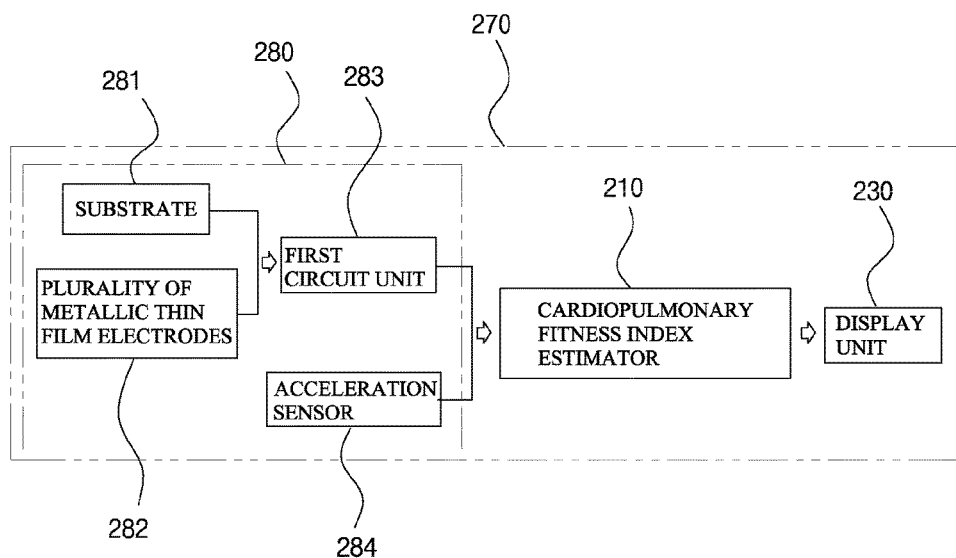

[FIG 23]
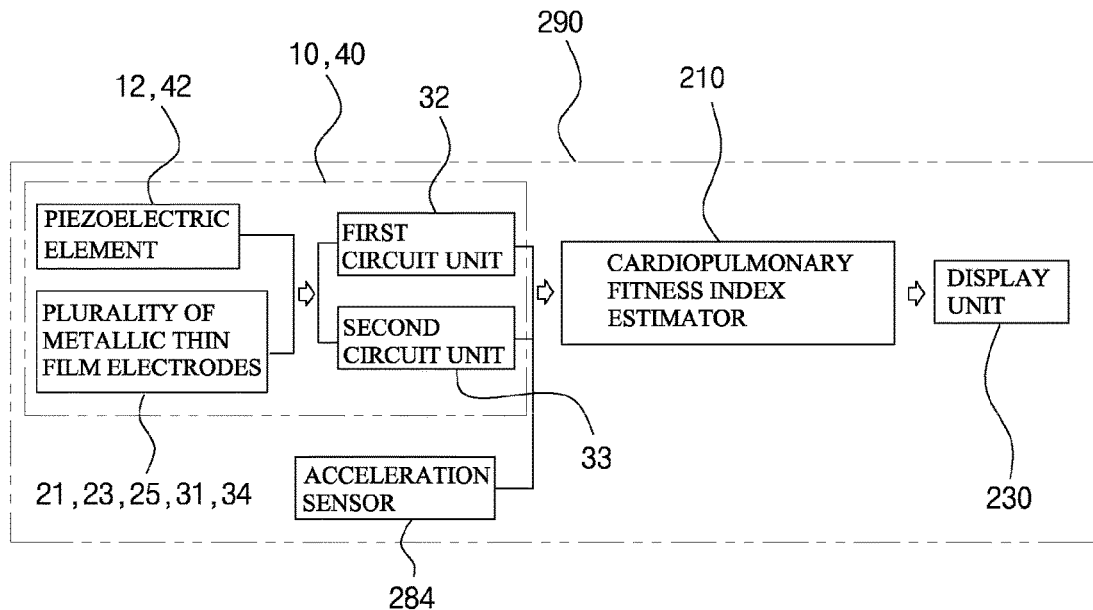
[FIG 24]
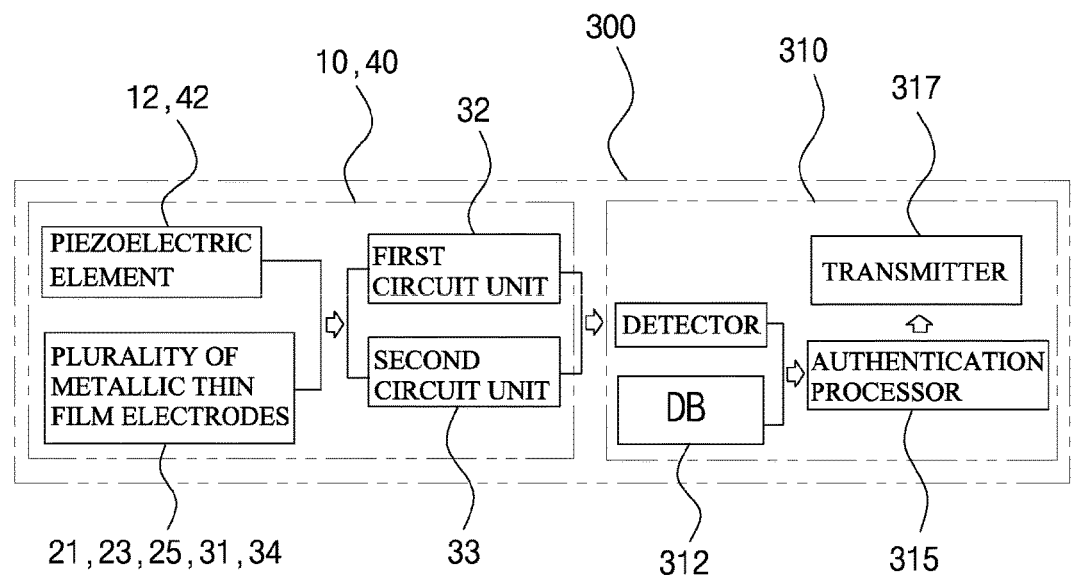

[FIG 25]
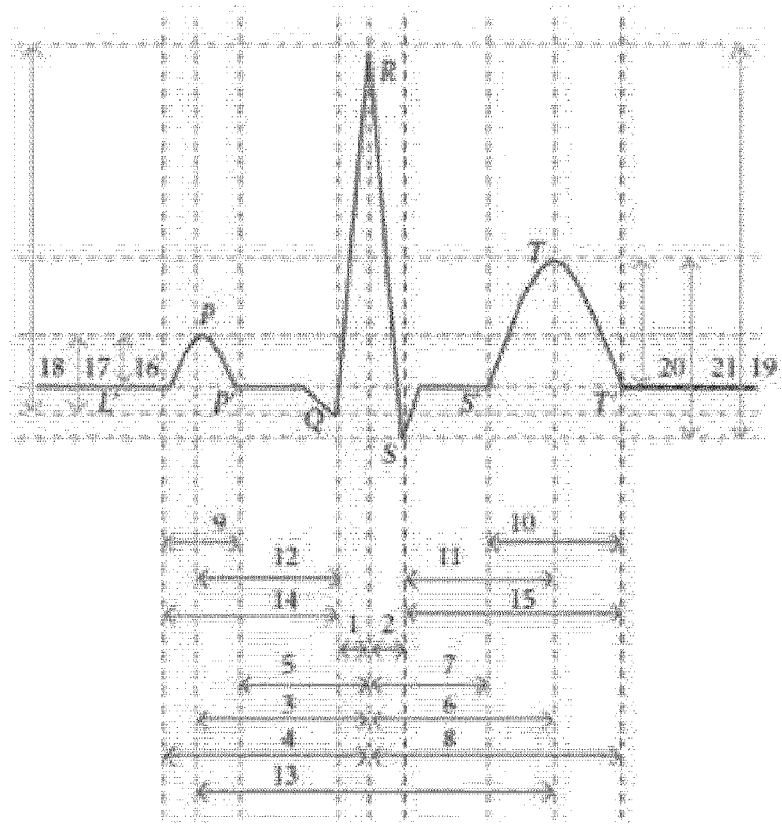
[FIG 26]
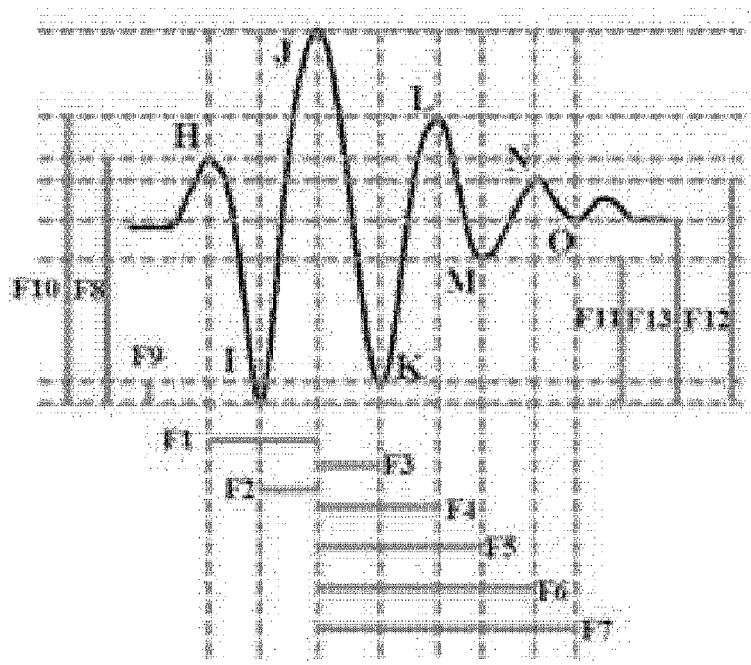

[FIG 27]
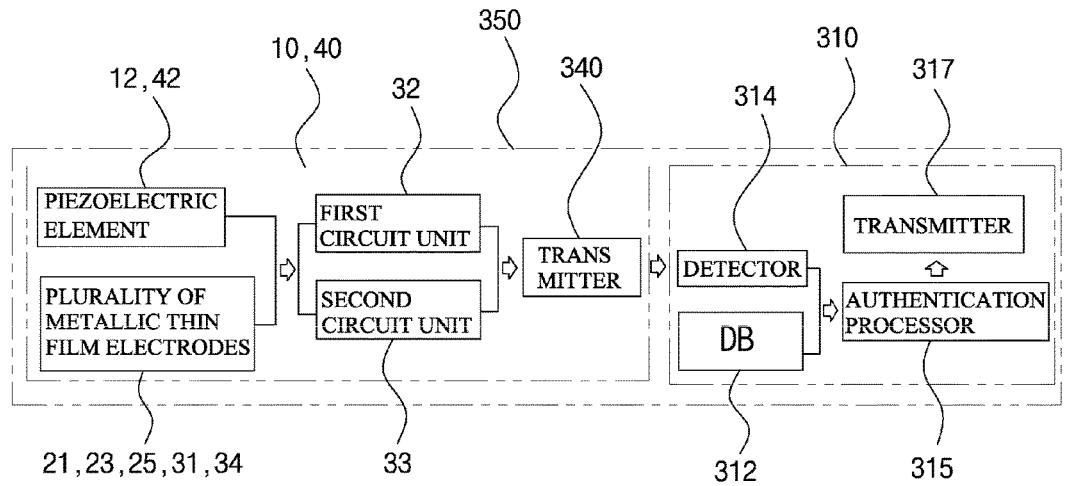
[FIG 28]
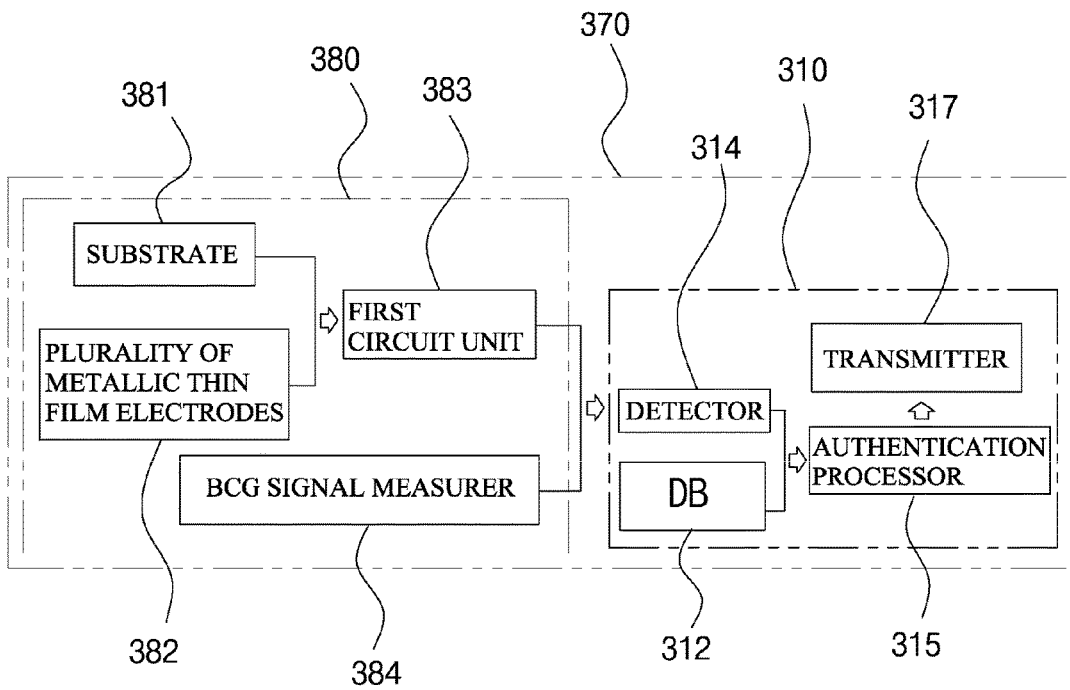

FILM-TYPE BIOMEDICAL SIGNAL MEASURING APPARATUS, BLOOD PRESSURE MEASURING APPARATUS USING THE SAME, CARDIOPULMONARY FITNESS ESTIMATING APPARATUS, AND PERSONAL AUTHENTICATION APPARATUS

CROSS REFERENCE TO PRIOR APPLICATIONS

This application is a National Stage Application of PCT International Patent Application No. PCT/KR2014/002469 filed on Mar. 24, 2014, under 35 U.S.C. § 371, which claims priority to Korean Patent Application Nos. 10-2013-0031220 filed on Mar. 24, 2013, 10-2014-0008619 filed on Jan. 23, 2014, 10-2014-0023359 filed on Feb. 27, 2014, and 10-2014-0033957 filed on Mar. 24, 2014, which are all hereby incorporated by reference in their entirety.

BACKGROUND OF THE INVENTION

Field of the Invention

Apparatuses and methods consistent with the present invention relate to a film-type biomedical signal measuring apparatus, and more particularly, to a film-type biomedical signal measuring apparatus that is configured in the form of a film to be easily attached to skin and to simultaneously measure two or more biomedical signals, a blood-pressure measuring apparatus and method for measuring blood pressure using the film-type biomedical signal measuring apparatus, a new-type cardiopulmonary fitness estimating apparatus and method for estimating a cardiopulmonary fitness index using the film-type biomedical signal measuring apparatus, and a personal authentication apparatus and method for determining whether a user is authenticated using the film-type biomedical signal measuring apparatus.

Description of the Related Art

For health examination of ordinary people as well as patients and elderly people, various biomedical signals such as electrocardiogram (ECG), ballistocardiogram (BCG), blood pressure, the amount of physical activity, a respiration rate, and maximal oxygen uptake ($VO_2max$) are required. However, most typical biomedical signal measuring apparatus are configured to separately measure these biomedical signals.

For example, an ECG measuring apparatus measures ECG by measuring an electrical signal of beating heart. In this regard, the ECG measuring apparatus is generally configured to measure an electrical signal of beating heart above the skin and has been widely used in hospitals. In hospitals, distortion, etc. of waveforms of ECG signals are analyzed to determine whether the heart is abnormal, and heat reaction according to various health indexes, for example, stress and motion load are checked simply using a heart rate. For ECG measurement, at least three electrodes up to 10 electrodes are attached onto a skin surface so as to measure ECG. In general, when ECG is measured using three electrodes, one electrode is used as a reference electrode and a potential difference between the remaining two electrodes is measured so as to measure ECG In addition, a BCG measuring apparatus measures physical reaction force of blood squirted during heartbeat on a skin surface to measure BCG, and biomedical indexes that is not present in ECG can be checked based on BCG. Accordingly, the BCG measuring apparatus have continuously received considerable attention by biomedical related researchers. For BCG measurement, BCG is measured by positioning a piezoelectric element between one part of a body, for example, sole and buttocks and a floor that contacts the body part and acquiring vertical vibration of the body according to blood flow as an electrical signal or positioning an acceleration sensor on the skin surface and measuring reaction of the body according to action of blood.

In addition, a body motion measuring apparatus measures body motion by quantitatively measuring a degree of movement of an acceleration sensor attached to each part such as an arm and a leg of the body to analyze the amount of physical activity, calorie consumption, step number, and so on. That is, the body motion measuring apparatus measures body motion by analyzing vibration of each part of the body according to body motion.

However, there are problems in that, an typical ECG measuring apparatus has a large size and a large number of wires, and thus it is cumbersome to use the apparatus and it is difficult to use the apparatus during movement, and even if the apparatus has a simple configuration, the apparatus is put around the chest in the form of a belt, and thus it is inconvenient to use the apparatus.

A typical BCG measuring apparatus measures BCG by positioning a wide and stiff paper type piezoelectric sensor on a wide body part such as a gap between buttock and a chair, between back and a chair, and between back and a bed or positioning a load cell type weight measuring sensor between a bed leg and the ground or in a weight scale, and thus there is a problem in that it is difficult to use the BCG measuring apparatus like the ECG measuring apparatus.

Most typical biomedical signal measuring apparatuses measure only one of biomedical signals such as ECG or BCG to provide only simple information, and thus there is a problem in that apparatuses according to respective biomedical signals need to be separately used to measure each biomedical signal.

In addition, among typical biomedical signal measuring apparatus, there is an apparatus for measuring a plurality of biomedical signals. There is a problem in that it is impossible to derive additional health information even if the apparatus for measuring a plurality of biomedical signals is used.

SUMMARY OF THE INVENTION

The present invention provides a film-type biomedical signal measuring apparatus that is configured in the form of a film so as to be easily attached to the skin and simultaneously measures two or more biomedical signals.

The present invention also provides an apparatus and method for measuring a blood pressure, for continuously measuring a blood pressure without limits of places using a film-type biomedical signal measuring apparatus that is configured in the form of a film so as to be easily attached to the skin and simultaneously measures an ECG signal and a BCG signal.

The present invention also provides a new type apparatus and method for estimating cardiopulmonary fitness, for very simply estimating a cardiopulmonary fitness index during a daily life using a film-type biomedical signal measuring apparatus that is configured in the form of a film so as to be easily attached to the skin and simultaneously measures an ECG signal and a BCG signal.

The present invention also provides a personal authentication apparatus and method for determining whether a user is authenticated using a film-type biomedical signal measuring apparatus that is configured in the form of a film so as to be easily attached to the skin and simultaneously measures an ECG signal and a BCG signal.

According to an aspect of the present invention, a film-type biomedical signal measuring apparatus includes a film-type piezoelectric element, a plurality of metallic thin film electrodes formed on the piezoelectric element, a first circuit unit for measuring a biomedical evoked potential from at least two of the plurality of metallic thin film electrodes, and a second circuit unit for measuring a biomedical evoked vibration signal from at least two of the plurality of metallic thin film electrodes.

A blood pressure measuring apparatus using the film-type biomedical signal measuring apparatus according to the present invention may include the film-type biomedical signal measuring apparatus and a blood pressure calculator for calculating a blood pressure using the ECG signal and the BCG signal that are measured by the first circuit unit and the second circuit unit, respectively.

A method for measuring a blood pressure using a film-type biomedical signal measuring apparatus according to the present invention may include simultaneously measuring an electrocardiogram (ECG) signal and a ballistocardiogram (BCG) signal, deriving an R-peak value of the simultaneously measured ECG signal and a J-peak value of the simultaneously measured BCG signal, deriving an R-J time interval between the derived R-peak value and J-peak value, and calculating the blood pressuring using the derived R-J time interval and a pre-stored blood pressure estimation regression equation for each user.

A cardiopulmonary fitness estimating apparatus using a film-type biomedical signal measuring apparatus according to the present invention may include the film-type biomedical signal measuring apparatus, and a cardiopulmonary fitness index estimator for estimating a cardiopulmonary fitness index using the ECG signal measured by the first circuit unit and the vibration signal measured by the second circuit unit.

A method for estimating cardiopulmonary fitness using a film-type biomedical signal measuring apparatus according to the present invention may include calculating and storing a heart rate and an amount of physical activity from the simultaneously and continuously measured ECG signal and human body motion signal, respectively at each unit time, extracting heart rate and amount of physical activity data in a period in which the heart rate increases from the stored heart rate and amount of physical activity data, detecting a regression equation between an amount of physical activity and a heart rate in which a period in which the heart rate increases using the extracted heart rate and amount of physical activity data, calculating maximum activity energy expenditure using the detected regression equation, and calculating maximal oxygen uptake ($VO_2$max) using the calculated maximum activity energy expenditure and a pre-stored maximal oxygen uptake estimation regression equation.

A personal authentication apparatus using a film-type biomedical signal measuring apparatus according to the present invention may include the film-type biomedical signal measuring apparatus, and a personal authentication unit for determining whether a user is authenticated using the ECG signal and the BCG signal that are measured by the first circuit unit and the second circuit unit, respectively.

A personal authentication method using a film-type biomedical signal measuring apparatus according to the present invention may include detecting an ECG fiducial value and a BCG fiducial value of an authentication target from the simultaneously ECG signal and BCG signal, respectively, and determining whether the user is authenticated by comparing the detected ECG fiducial value and BCG fiducial value of the authentication target with a pre-stored ECG fiducial value and BCG fiducial value of the registration, respectively.

ADVANTAGEOUS EFFECTS

The film-type biomedical signal measuring apparatus according to the present invention may be configured in such a way that a plurality of metallic thin film electrodes and a circuit unit are formed on a film-type piezoelectric element in order to measure a biomedical signal, and thus the overall configuration of the apparatus is very simple in the form of a film so as to be easily attached to the skin of a human body and enhance usability convenience.

The film-type biomedical signal measuring apparatus according to the present invention may simultaneously measure a vibration signal as a well as an electrical signal of a human body using a plurality of metallic thin film electrodes and a circuit unit that are formed on a piezoelectric element.

The film-type biomedical signal measuring apparatus according to the present invention may simultaneously measure ECG and BCG from the simultaneously measured electrical signal and vibration signal of the human body and may extract biomedical information of various types of health indexes such as a heart rate, a stress index, BCG, a blood pressure, an amount of physical activity, a respiration rate, and $VO_2$max from the two different biomedical signals.

According to an apparatus and method for measuring a blood pressure according to the present invention, the apparatus may be configured in the form of a film so as to be easily attached to the skin and may measure a blood pressure using a film-type biomedical signal measuring apparatus for simultaneously measuring an ECG signal and a BCG signal, and thus a blood pressure may be continuously measured without limits of places.

According to an apparatus and method for estimating cardiopulmonary fitness according to the present invention, the apparatus may be configured in the form of a film so as to be easily attached to the skin and may estimate a cardiopulmonary fitness index using a film-type biomedical signal measuring apparatus for simultaneously measuring an ECG signal and a BCG signal. Accordingly, a system and method for measuring cardiopulmonary fitness according to the present invention may easily and simply estimate a cardiopulmonary fitness index during a daily life using the film-type biomedical signal measuring apparatus to be easily attached to the skin, and thus personal physical health as well as personal physical activity may be managed by continuously measuring and managing a cardiopulmonary fitness index, thereby highly helping personal health maintenance.

According to a system and method for estimating cardiopulmonary fitness according to the present invention, cardiopulmonary fitness is not necessarily measured through intended sub-maximal exercise unlike a conventional measuring apparatus, and thus cardiopulmonary fitness of patients and elderly people as well as healthy people may also be easily and safely measured.

A personal authentication apparatus and method according to the present invention may determine whether a user is authenticated using a film-type biomedical signal measuring apparatus for simultaneously measuring an ECG signal and a BCG signal, and thus whether the user is authenticated may be determined by multiply using the ECG and the BCG, thereby enhancing the accuracy of personal authentication.

According to a personal authentication apparatus and method according to the present invention, since whether a user is authenticated may be determined using a film-type biomedical signal measuring apparatus that is configured in the form of a film so as to be easily attached to the skin, the personal authentication apparatus may continuously determine whether the user is authenticated in real time without limits of places while being attached to the skin during a daily life, and thus the personal authentication apparatus may be used as a biomedical signal-based personal authentication sensor.

It will be appreciated by persons skilled in the art that that the effects that could be achieved with the present invention are not limited to what has been particularly described hereinabove and other advantages of the present invention will be more clearly understood from the following detailed description taken in conjunction with the accompanying drawings.

BRIEF DESCRIPTION OF THE DRAWING FIGURES

FIGS. 1 and 2 are diagrams illustrating a measuring apparatus according to an embodiment of the present invention, FIG. 1 is a schematic plan view illustrating an attachment surface of a piezoelectric element, and FIG. 2 is a schematic plan view of an opposite surface of the piezoelectric element.

FIGS. 3 to 6 are diagrams illustrating a film-type biomedical signal measuring apparatus according to another embodiment of the present invention, FIG. 3 is a schematic cross-sectional view of the measuring apparatus, FIG. 4 is a schematic plan view illustrating an attachment surface of a piezoelectric element, FIG. 5 is a schematic plan view illustrating an opposite surface of the piezoelectric element, and FIG. 6 is a schematic plan view illustrating a formation surface of a substrate.

FIG. 7 is a schematic circuit diagram illustrating an example of the first circuit according to an embodiment of the present invention, and FIG. 8 a schematic circuit diagram illustrating an example of the second circuit unit according to an embodiment of the present invention.

FIGS. 9 and 10 are images of an example of a measuring apparatus according to an embodiment of the present invention, FIG. 9 is an image of a state in which an attachment surface of a piezoelectric element is directed upward, and FIG. 10 is an image of a state in which a formation surface of a substrate is directed upward when the measuring apparatus further includes an opposite surface of a piezoelectric element or a substrate.

FIG. 11 is a schematic diagram illustrating a configuration of a blood pressure measuring apparatus according to an embodiment of the present invention, FIG. 12 is a graph showing a relation between an R-J time interval and a systolic blood pressure, FIGS. 13 to 15 are graphs illustrating a relation between an R-J time interval and a SBP, which is different for each respective user, FIG. 16 is a schematic diagram illustrating a blood pressure measuring apparatus according to an embodiment of the present invention, and FIG. 17 is a schematic diagram illustrating a configuration of a blood pressure measuring apparatus for measuring a BCG signal using an acceleration sensor according to an embodiment of the present invention.

FIG. 18 is a schematic diagram illustrating a cardiopulmonary fitness estimating apparatus according to an embodiment of the present invention, FIG. 19 is a graph illustrating heart rate (HR (BPM), beat/min) and an amount of physical activity that are calculated and stored every one minute from continuously measured ECG signals and vibration signals, FIG. 20 is a graph illustrating detection of a linear regression equation by extracting only heart rate and amount of physical activity data in a period in which a heart rate increases, FIG. 21 is a schematic diagram illustrating a configuration of a cardiopulmonary fitness measuring system according to another embodiment of the present invention, FIG. 22 is a schematic diagram illustrating a configuration of a cardiopulmonary fitness estimating apparatus for measuring a human body motion signal using only an acceleration sensor without using a vibration signal of a piezoelectric element, according to an embodiment of the present invention, and FIG. 23 is a schematic diagram illustrating a cardiopulmonary fitness measuring system that uses a vibration signal of a piezoelectric element and further includes an acceleration sensor, according to an embodiment of the present invention. and FIG. 24 is a schematic diagram illustrating a configuration of a personal authentication apparatus according to an embodiment of the present invention, FIG. 25 is a graph illustrating an example of ECG fiducial values detected from an ECG signal, FIG. 26 is a graph illustrating an example of BCG fiducial values detected from a BCG signal, FIG. 27 is a schematic diagram illustrating a configuration of a personal authentication apparatus 350 according to another embodiment of the present invention, and FIG. 28 is a schematic diagram illustrating a personal authentication apparatus for measuring a BCG signal using an acceleration sensor, according to an embodiment of the present invention.

DETAILED DESCRIPTION OF THE EXEMPLARY EMBODIMENTS

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention.

The present invention relates to a film-type biomedical signal measuring apparatus configured in a such a way that a plurality of metallic thin film electrodes and a circuit unit are formed on a film-type piezoelectric element so as to easily attach the apparatus to the skin and an electrical signal as well as an electrical signal of a human body is simultaneously measured using the plurality of metallic thin film electrodes and the circuit unit. Accordingly, the film-type biomedical signal measuring apparatus according to the present invention may simultaneously measures electrocardiogram (ECG) and ballistocardiogram (BCG) from the simultaneously measured electrical signal and vibration signal of the human body and extract biomedical information of various types of health indexes such as a heart rate, a stress index, BCG, a blood pressure, an amount of physical activity, a respiration rate, and $VO_2$max from the two different biomedical signals.

A film-type biomedical signal measuring apparatus according to an embodiment of the present invention may include a film-type piezoelectric element, at least two first metallic thin film electrodes formed on one surface (which is a surface attached to the skin for measuring a biomedical signal, and hereinafter, referred to as an 'attachment surface') of the film-type piezoelectric element so as not to be electrically connected to each other, a second metallic thin film electrode formed on another surface (which is an opposite surface of the surface attached to the skin for measuring the biomedical signal, and hereinafter, referred to as an "opposite surface') of the film-type piezoelectric element, a first circuit unit, and a second circuit unit.

The piezoelectric element is a component that is formed of a piezoelectric material with a piezoelectric effect whereby electrical polarization is caused on an external surface of a crystal when a force is applied to solid. In this regard, when the piezoelectric element is inserted between metallic plates, sound, vibration, pressure, and so on may be detected. For example, when a pressure is applied to the piezoelectric element, electricity is generated in the piezoelectric element. In this case, a pressure applied to the piezoelectric element may be measured by measuring change in electricity quantity, which occurs when pressure is applied to the piezoelectric element. The piezoelectric material uses a principle whereby a potential difference (voltage) is generated when pressure is applied to the material and may be, for example, quartz, Rochelle slat, barium titanate (BaTiO), or artificial ceramic (PZT).

The present invention uses a piezoelectric element so as to measure pressure, vibration, and so on, which are detected from the skin of a human body, as well as an electrical signal of the human body, and in particular, uses a film-type thin piezoelectric element and forms a metallic thin film electrode on an attachment surface of the film-type piezoelectric element so as to easily attach the apparatus to the skin during measurement of the biomedical signal.

According to the present invention, a plurality of, that is, at least two independent first metallic thin film electrodes that are not electrically connected to each other may be formed on an attachment surface of a piezoelectric element so as to measure pressure, vibration, and so on detected from the skin of a human body and to also measure an electrical signal of the human body. Here, at least two first metallic thin film electrodes are formed on the attachment surface of the piezoelectric element because a potential difference between at least two electrodes needs to be measured in order to measure the electrical signal of the human body. In addition, three or more first metallic thin film electrodes may be formed on the attachment surface of the piezoelectric element in order to more precisely measure a biomedical signal such as electrocardiogram (ECG). For ECG measurement, a minimum of two electrodes need to be used in order to measure a potential difference at a minimum of two points of the human body in order to measure an electrical signal of a beating heart, and a minimum of 10 electrodes may be used in order to more precisely measure ECG. Accordingly, the film-type biomedical signal measuring apparatus according to the present invention may be configured in such a way that at least two first metallic thin film electrodes are formed on the attachment surface of the piezoelectric element, and the present invention is not limited to the number of the first metallic thin film electrodes.

According to the present invention, a second metallic thin film electrode may be formed on an opposite surface of the piezoelectric element so as to measure pressure, vibration, and so on of a human body as well as an electrical signal of the human body. In general, in order to measure pressure, vibration, and so on, the piezoelectric element needs to be position between metallic plates and change in electricity quantity that occurs when a pressure is applied to the piezoelectric element needs to be measured, and thus according to the present invention, the second metallic thin film electrode may be formed on the opposite surface of the piezoelectric element. Here, electrodes between which piezoelectric elements are positioned in order to measure pressure, vibration, and so on and that face the second metallic thin film electrode may use at least one of at least two first metallic thin film electrodes formed on the attachment surface of the piezoelectric element.

That is, in the film-type biomedical signal measuring apparatus according to the present invention, a first metallic thin film electrode for measuring an electrical signal and a first metallic thin film electrode for measuring pressure, vibration, and so on may be formed on the attachment surface of the piezoelectric element. In this case, the first metallic thin film electrode for measuring pressure, vibration, and so on may also be used as a first metallic thin film electrode for measuring the electrical signal. However, the present invention is not limited thereto. Thus, the first metallic thin film electrode for measuring pressure and so on may be formed separately from the first metallic thin film electrode for measuring the electrical signal, and in this case, at least three first metallic thin film electrodes need to be formed on the attachment surface of the piezoelectric element.

According to the present invention, a first circuit unit and second circuit unit, for measuring a biomedical evoked potential and vibration signal of a human body from the first metallic thin film electrode and the second metallic thin film electrode formed on the attachment surface of the piezoelectric element, may be formed on the opposite surface of the piezoelectric element. That is, the first circuit unit may measure a biomedical evoked potential of the human body and the second circuit unit may measure a biomedical evoked vibration signal of the human body.

The first circuit unit may be formed on the opposite surface of the piezoelectric element so as to be electrically connected to at least one two of the first metallic thin film electrodes so as to measure a potential difference between the at least two first metallic thin film electrodes. In addition, when the first circuit unit is configured to measure a potential difference between the at least two of the first metallic thin film electrodes formed on the attachment surface of the piezoelectric element, a biomedical evoked potential of a human body may be measured from the potential difference so as to measure a biomedical signal such as ECG The second circuit unit may be formed on the opposite surface of the piezoelectric element so as to be electrically connected to at least one of the first metallic thin film electrodes and the second metallic thin film electrode and may be configured to measure quantity of charge of the piezoelectric element from the at least one first metallic thin film electrode and the second metallic thin film electrode. In addition, when the second circuit unit is configured to measure quantity of charge of the piezoelectric element, change in electricity quantity, which occurs when pressure is applied to the piezoelectric element due to pressure, vibration, and so on of the human body, may be measured, and accordingly, a biomedical evoked vibration signal of the human body may be measured so as to measure a biomedical signal such as BCG, amount of physical activity, and so on. Here, the first metallic thin film electrode that is electrically connected to the second circuit unit may be a reference electrode for measurement of quantity of charge of the piezoelectric element along with the second metallic thin film electrode, and in this case, the first metallic thin film electrode as a reference electrode may use all, some, or one of first metallic thin film electrodes formed on the attachment surface of the piezoelectric element, and accordingly, the number of the first metallic thin film electrodes that are electrically connected to the second circuit unit may be changed, but the present invention is not limited thereto.

The at least two first metallic thin film electrodes and the first circuit unit may be electrically connected by a conductive material filled in a through hole formed in the piezoelectric element. Then the first metallic thin film electrode and the first circuit unit that are respectively formed on the attachment surface and the opposite surface across the piezoelectric element may be easily electrically connected to each other. Here, the conductive material filled in the through hole may be any material through which electricity passes, such as conductive epoxy, metallic rivet, and soldering, but in particular, the conductive material may be conductive epoxy in consideration of the fact that the material is filled in the through hole formed in the film-type piezoelectric element.

The at least one of the first metallic thin film electrodes and the second circuit unit may be electrically connected to each other by a conductive material filled in the through hole formed in the piezoelectric element, and the second metallic thin film electrode and the second circuit unit may be electrically connected to each other by a metallic thin film formed on an opposite surface of the piezoelectric element. Then, the first metallic thin film electrode and the second circuit unit that are respectively formed on the attachment surface and the opposite surface across the piezoelectric element may be easily electrically connected to each other by the conductive material filled in the through hole, and the second metallic thin film electrode and the second circuit unit formed on the same surface that is the opposite surface of the piezoelectric element may be easily electrically connected to each other by a metallic thin film formed on the opposite surface of the piezoelectric element. Here, the metallic thin film for electrical connection between the second metallic thin film electrode and the second circuit unit may be formed together when a metallic thin film pattern for configuring the first circuit unit and the second circuit unit may be formed, and the first metallic thin film electrode and the second circuit unit may be electrically connected through the conductive material filled in the through hole, and alternatively the second circuit unit may be electrically connected to the first metallic thin film electrode through a through hole by connecting the second circuit unit to the first circuit unit that is electrically pre-connected to the first metallic thin film electrode by the metallic thin film.

The first circuit unit may include an operational amplifier (op-amp) disposed between any one of the first metallic thin film electrodes and another one of the first metallic thin film electrodes so as to measure a potential difference between the two first metallic thin film electrodes that are electrically connected to each other.

The first circuit unit may be configured to simply measure a potential difference between the two first metallic thin film electrodes, and alternatively, when three or more first metallic thin film electrodes are formed on the attachment surface of the piezoelectric element, the first circuit unit may be configured to selectively measure a potential difference between two of the three or more first metallic thin film electrodes. Accordingly, an electrical signal of the human body may be more precisely measured so as to more precisely measure a biomedical signal such as ECG A film-type biomedical signal measuring apparatus according to an embodiment of the present invention includes a film-type piezoelectric element with one surface (hereinafter, referred to as an 'attachment surface') on which at least two first metallic thin film electrodes formed so as not to be electrically connected to each other and the other surface (hereinafter, referred to as an 'opposite surface') on which a second metallic thin film electrode is formed, and a film-type substrate with any surface (which is an adhesion surface adhered to the piezoelectric element, and hereinafter, referred to as an 'adhesion surface') that is adhered to the opposite surface of the piezoelectric element, and a first circuit unit that is electrically connected to at least two of the first metallic thin film electrodes and measures a potential difference between the at least two first metallic thin film electrodes, a third metallic thin film electrode electrically connected to any one of the first metallic thin film electrodes, and a second circuit unit that is electrically connected to the second metallic thin film electrode and the third metallic thin film electrode so as to measure quantity of charge of the piezoelectric element from the first metallic thin film electrode, the third metallic thin film electrode, and the second metallic thin film electrode may be formed on another surface (which is an opposite surface of the adhesion surface, and hereinafter, referred to as a 'formation surface') of the film-type substrate.

That is, compared to the measuring apparatus according to the above embodiment in which the first metallic thin film electrode, the second metallic thin film electrode, the first circuit unit, and the second circuit unit are formed on the attachment surface and the opposite surface of one piezoelectric element, the film-type biomedical signal measuring apparatus according to the present embodiment may further include a separate film-type flexible substrate attached to the opposite surface of the piezoelectric element, and the first metallic thin film electrode and the second metallic thin film electrode may be formed on the attachment surface and the opposite surface of the piezoelectric element, the remaining first circuit unit and second circuit unit may be formed on a formation surface of the substrate, and a third metallic thin film electrode electrically connected to at least one of first metallic thin film electrodes may be further formed on the formation surface of the substrate.

According to the above measuring apparatus according to the present embodiment, since one of two electrodes as reference electrodes for measuring quantity of charge of the piezoelectric element may be at least one first metallic thin film electrode formed on the attachment surface of the piezoelectric element that is electrically connected to the third metallic thin film electrode and the third metallic thin film electrode that are formed on the formation surface of the substrate, and the other may be the second metallic thin film electrode formed on the opposite surface of the piezoelectric element, the second metallic thin film electrode as one of the reference electrodes are surrounded between the first metallic thin film electrode and third metallic thin film electrode as the other one of the reference electrodes, and for example, a sandwich-type shield structure may be achieved to accordingly remove noise piezoelectric element so as to more precisely measure the quantity of charge, and thus change in quantity of charge of the piezoelectric element may be more sensitively measured according to pressure, vibration, and so on of the human body.

In the measuring apparatus according to the present embodiment, the piezoelectric element and the substrate may be adhered by adhesives or double-sided adhesive tapes, and another separate member may be interposed between the piezoelectric element and the substrate in order to insulate therebetween and maintain robustness, but the present invention is not limited thereto.

The at least two first metallic thin film electrodes and the first circuit unit may be electrically connected by a conductive material filled in a through hole formed on the piezoelectric element and the substrate, the at least one first metallic thin film electrode and the third metallic thin film electrode may be electrically connected to each other through a conductive material filled in a through hole formed on the piezoelectric element and the substrate, the second metallic thin film electrode and the second circuit unit may be electrically connected to each other through a conductive material filled in a through hole formed on the substrate, and the third metallic thin film electrode and the second circuit unit may be electrically connected to each other by a metallic thin film formed on the other surface of the substrate.

In addition, the first circuit unit may be configured to selectively measure a potential difference between the two first metallic thin film electrodes among the at least two first metallic thin film electrodes, as described above. The detailed description in the aforementioned embodiments is applied to a detailed description of the other components of the present embodiment.

A film-type biomedical signal measuring apparatus according to another embodiment of the present invention may include a film-type piezoelectric element with one surface (hereinafter, referred to as an 'attachment surface') on which at least three metallic thin film electrodes are formed and another surface (hereinafter, referred to as an 'opposite surface') on which a second metallic thin film electrode is formed, and a film-type substrate with any surface (hereinafter, referred to as an 'adhesion surface') adhered to the opposite surface of the piezoelectric element, and a first circuit unit formed on an opposite surface (hereinafter, referred to as a 'formation surface') of the adhesion surface so as to be electrically connected to the remaining first metallic thin film electrodes except for any one of first metallic thin film electrodes so as to measure a potential difference between the remaining first metallic thin film electrodes, a third metallic thin film electrode formed on the formation surface so as to be electrically connected to any one of first metallic thin film electrodes, and a second circuit unit formed on the formation surface so as to be electrically connected to the second metallic thin film electrode and the third metallic thin film electrode and configured to measure the quantity of charge of the piezoelectric element from the any one first metallic thin film electrode, the third metallic thin film electrode, and the second metallic thin film electrode may be formed on the substrate.

The first circuit unit may be electrically connected to the third metallic thin film electrode and may be configured to measure a potential difference between the remaining first metallic thin film electrodes using the any one first metallic thin film electrode as a reference electrode.

In the measuring apparatus according to the present embodiment, at least three first metallic thin film electrodes may be formed on the attachment surface of the piezoelectric element, and the first circuit unit may measure a potential difference between the remaining first metallic thin film electrodes using any one of the at least three first metallic thin film electrodes as a reference electrode to accordingly enable precise measurement, and accordingly, an electrical signal of a human body may be more precisely measured, thereby enhancing the accuracy of ECG measurement.

The remaining first metallic thin film electrode and the first circuit unit may be electrically connected to each other through a conductive material filled in a through hole formed in the piezoelectric element and the substrate, the any one first metallic thin film electrode and the third metallic thin film electrode may be electrically connected to each other through a conductive material filled in a through hole formed in the piezoelectric element and the substrate, the second metallic thin film electrode and the second circuit unit may be electrically connected to each other through a conductive material filled in a through hole formed in the substrate, and the third metallic thin film electrode and the first circuit unit, and the third metallic thin film electrode and the second circuit unit may be electrically connected to each other through a metallic thin film formed on the other one surface of the substrate.

In addition, the first circuit unit may be configured to selectively measure a potential difference between two first metallic thin film electrodes among the remaining first metallic thin film electrodes, as described above. The detailed description in the aforementioned embodiments is applied to a detailed description of the other components of the present embodiment.

In the measuring apparatus according to the present embodiment, the first circuit unit and the second circuit unit commonly uses one first metallic thin film electrode so as to be accordingly simplified, and since the first metallic thin film electrode to be used as a first circuit unit may be electrically connected to the third metallic thin film electrode that is electrically connected to the first metallic thin film electrode, a metallic thin film for electrical connection between the first circuit unit and the third metallic thin film electrode is formed without a separate through hole during formation of a metallic thin film pattern for formation of the first circuit unit and the second circuit unit on the formation surface of the substrate, thereby accordingly simplifying the configuration and a manufacturing method.

The film-type biomedical signal measuring apparatus according to an embodiment of the present invention may further include an adhesive member for easily attaching the attachment surface of the piezoelectric element to the skin so as to be included in the attachment surface of the piezoelectric element or to surround the piezoelectric element or the substrate. The adhesive member may be silicon, PDMS, or the like.

The film-type biomedical signal measuring apparatus according to an embodiment of the present invention may further include a storage unit for storing signals measured by the first circuit unit and the second circuit unit and a transmitter for transmitting the signal out of the measuring apparatus. Here, the transmitter may be configured by wire, wirelessly, or wired/wireless.

The above film-type biomedical signal measuring apparatus according to the present invention may be configured in the form of a film to constitute a simple configuration so as to be easily attached to the skin and enhance usability convenience. The film-type biomedical signal measuring apparatus according to the present invention may simultaneously measure an electrical signal, pressure, vibration, and so on of a human body while being attached to the skin and may extract biomedical information of various types of health indexes such as a heart rate, a stress index, BCG, a blood pressure, an amount of physical activity, a respiration rate, and $VO_2$max from the two different biomedical signals. The film-type biomedical signal measuring apparatus according to the present invention may additionally calculate heart rate, stress index, BCG, blood pressure, amount of physical activity, respiration rate, CPF, $VO_2$max, and so on using a plurality of biomedical signals while simply measuring the plurality of biomedical signals, and thus various health indexes may be easily managed.

Reference will now be made in detail to example embodiments, examples of which are illustrated in the accompanying drawings. In the drawings, the thicknesses of layers and regions are exaggerated for clarity, and thus the present invention is not limited by the relative size or thickness of the drawings.

FIGS. 1 and 2 are diagrams illustrating a measuring apparatus 10 according to an embodiment of the present invention. FIG. 1 is a schematic plan view illustrating an attachment surface of a piezoelectric element and FIG. 2 is a schematic plan view of an opposite surface of the piezoelectric element.

Referring to FIGS. 1 and 2, the measuring apparatus 10 according to an embodiment of the present invention may include a film-type piezoelectric element 12, three first metallic thin film electrodes 21, 23, and 25 formed on an attachment surface of the piezoelectric element 12, a second metallic thin film electrode 31 formed on the opposite surface of the piezoelectric element 12, and a first circuit unit 32 and a second circuit unit 33 which are formed on the opposite surface of the piezoelectric element 12.

The first circuit unit 32 may be used to measure a potential difference between the first metallic thin film electrodes 21, 23, and 25 and may be electrically connected to the first metallic thin film electrodes 21, 23, and 25 through a conductive material 27 charged in through holes 22, 24, and 26 formed in the piezoelectric element 12.

The second circuit unit 33 may be used to measure quantity of charge of the piezoelectric element 12 from any one electrode 21 of the first metallic thin film electrodes 21, 23, and 25 and the second metallic thin film electrode 31 and may be electrically connected to each of the electrode 21 and the second metallic thin film electrode 31 through the through hole 22 formed in the piezoelectric element 12 and a metallic thin film 28 formed on the opposite surface of the piezoelectric element 12.

The three first metallic thin film electrodes 21, 23, and 25 may include a reference electrode 21 for setting reference potential during measurement of a potential difference and potential difference measuring electrodes 23 and 25 for measurement of a potential difference. In particular, the reference electrode 21 may be commonly used with the any one electrode 21 as a reference electrode for measurement of the quantity of charge of the piezoelectric element 12 by the second circuit unit 33.

The second circuit unit 33 and the any one electrode 21 as the reference electrode 21 may be electrically connected through a first through hole 22 formed in the piezoelectric element 12 and the conductive material 27 charged in the first through hole 22, and the first circuit unit 32 and each of the potential difference measuring electrodes 23 and 25 may be electrically connected through a second through hole 24 and a third through hole 26 which are formed in the piezoelectric element 12 and the conductive material 27 charged in the first and second through holes 24 and 26.

Although not illustrated in the drawing, the first circuit unit 32 and the reference electrode 21 may be electrically connected through a separate through hole and a conductive material charged in the through hole or may be electrically connected by circuit connecting the first circuit unit 32 to the second circuit unit 33 that is electrically connected to the reference electrode 21.

A non-formation region 14 in which a metallic thin film is not formed may be formed on the attachment surface of the piezoelectric element 12 so as to prevent the first metallic thin film electrodes 21, 23, and 25 from being electrically connected. In addition, the through holes 22, 24, and 26 may be formed in regions in which the first metallic thin film electrodes 21, 23, and 25 are formed, but the through holes 22, 24, and 26 may be formed to be spaced apart from the regions for formation of the first metallic thin film electrodes 21, 23, and 25 by a predetermine distance by extension regions 29, as illustrated in the drawing.

As in the present embodiment, a film-type biomedical signal measuring apparatus 10 according to the present invention may be configured to use only the reference electrode 21 as a reference electrode for measuring quantity of charge of the piezoelectric element 12, but according to another embodiment of the present invention, a film-type biomedical signal measuring apparatus may be configured to use, as a reference electrode, all the first metallic thin film electrodes 21, 23, and 25 formed on the attachment surface of the piezoelectric element 12 in order to precisely measure change in quantity of charge of the piezoelectric element 12.

FIGS. 3 to 6 are diagrams illustrating a film-type biomedical signal measuring apparatus 40 according to another embodiment of the present invention. FIG. 3 is a schematic cross-sectional view of the measuring apparatus 40, FIG. 4 is a schematic plan view illustrating an attachment surface of a piezoelectric element, FIG. 5 is a schematic plan view illustrating an opposite surface of the piezoelectric element, and FIG. 6 is a schematic plan view illustrating a formation surface of a substrate.

With regard to the description of the measuring apparatus 40 according to the present embodiment, for convenience of description, the reference numerals and detailed description in the aforementioned embodiment may be applied in the same way to the reference numerals and detailed descriptions of the same components as those of the measuring apparatus 10 according to the aforementioned embodiment among components of the measuring apparatus 40.

Referring to FIGS. 3 to 6, the measuring apparatus 40 according to the present embodiment may include a piezoelectric element 42, a film-type flexible substrate 50 adhered to the opposite surface of the piezoelectric element 42, and an adhesive member 43 for adhesion between the piezoelectric element 12 and the substrate 50. The adhesive member 43 may be adhesives or double-sided adhesive tapes.

The three first metallic thin film electrodes 21, 23, and 25 may be formed on the attachment surface of the piezoelectric element 42, the second metallic thin film electrode 31 may be formed on the opposite surface of the piezoelectric element 42, and a third metallic thin film electrode 34, the first circuit unit 32, and the second circuit unit 33 may be formed on the formation surface of the substrate 50 as an opposite surface of an adhesive surface of the substrate 50 adhered to the opposite surface of the piezoelectric element 42.

The three first metallic thin film electrodes 21, 23, and 25 may include the reference electrode 21 for reference potential setting during measurement of a potential difference and the potential difference measuring electrodes 23 and 25 for measuring the potential difference, and the first circuit unit 32 and each of the potential difference measuring electrodes 23 and 25 may be electrically connected through the second through hole 24 and the third through hole 26 which are formed in the piezoelectric element 12 and the substrate 50, and the conductive material 27 filled in the second and third through holes 24 and 26.

The third metallic thin film electrode 34 and the reference electrode 21 may be electrically connected through a fourth through hole 44 formed in the piezoelectric element 42 and the substrate 50 and the conductive material 27 charged in the fourth through hole 44, the third metallic thin film electrode 34 and the second circuit unit 33 may be electrically connected through a metallic thin film 45 formed on the formation surface of the substrate 50, and the second metallic thin film electrode 31 and the second circuit unit 33 may be electrically connected through a fifth through hole 46 formed in the substrate 50 and the conductive material 27 charged in the fifth through hole 46.

Although not illustrated in the drawing, the first circuit unit 32 may be electrically connected directly to the reference electrode 21 through a separate through hole and a conductive material charged in the through hole, may be electrically connected to the reference electrode 21 by electrically connecting the first circuit unit 32 to the third metallic thin film electrode 34 by a metallic thin film that is separately formed on the formation surface of the substrate 50 like in the case in which the second circuit unit 33 and the third metallic thin film electrode 34 are electrically connected by the metallic thin film 45, or may be electrically connected to the reference electrode 21 by circuit connecting the first circuit unit 32 to the second circuit unit 33 that is electrically connected to the reference electrode 21 through the third metallic thin film electrode 34.

As illustrated in FIG. 5, a non-formation region 47 in which a metallic thin film is not formed may be formed on the opposite surface of the piezoelectric element 42 so as to prevent the second, third, and fourth through holes 24, 26, and 44 from being electrically connected.

The measuring apparatus 40 with the aforementioned configuration according to the present embodiment is configured in such a way that the second metallic thin film electrode 31 as one of reference electrodes for measuring the quantity of charge of the piezoelectric element 42 is disposed between the third metallic thin film electrode 34 and the reference electrode 21 constituting another reference electrode, and accordingly noise may be removed so as to more precisely measure the quantity of charge of the piezoelectric element 42.

Although not illustrated, as described above, a film-type biomedical signal measuring apparatus according to the present invention may include an adhesive member formed of silicon, PDMS, or the like, which facilitates skin attachment, a storage unit for storing signals measured by a first circuit unit and a second circuit unit, and a transmitter for transmitting the signals out of the measuring apparatus.

The adhesive member may be configured to entirely surround the measuring apparatus so as to function as a cover for protection of the measuring apparatus while facilitating skin attachment of the measuring apparatus.

FIGS. 7 and 8 are schematic diagrams illustrating configurations of a first circuit unit and a second circuit unit according to an embodiment of the present invention. FIG. 7 is a schematic circuit diagram illustrating an example of the first circuit unit configured to measure an electrocardiogram (ECG) signal from a measured potential difference and FIG. 8 is a schematic circuit diagram illustrating an example of the second circuit unit configured to measure a ballistocardiogram (BCG) signal from measured quantity of charge of a piezoelectric element.

Referring to FIG. 7, the first circuit unit according to an embodiment of the present invention may include two potential difference measuring electrode units ⓐ, a pre-amp circuit unit ⓑ for extracting a potential difference of skin surfaces from the two potential difference measuring electrode units, a potential difference measuring circuit unit ⓒ for measuring a potential difference of the two potential difference measuring electrode units from potential of the two skin surfaces, and a filter circuit unit ⓓ for filtering the measured potential difference and extracting only an ECG signal.

Here, the pre-amp circuit unit ⓑ is a circuit unit required for signal acquisition when an electrode does not contact directly a human body due to other materials (e.g., adhesive gel or clothes) between the electrode and the human body like in the case in which the adhesive member entirely surrounds the measuring apparatus.

Referring to FIG. 8, the second circuit unit according to an embodiment of the present invention may include two electrode units ⓔ for BCG measurement and a circuit unit ⓕ for changing quantity of charge charged in the BCG measuring electrodes into a voltage signal and filter the voltage signal.

The first circuit unit and the second circuit unit may be configured to measure change in potential of electrodes connected to the measuring apparatus and to derive, store, and transmit the measured potential change and configured together with a power source (a battery).

In the measuring apparatus according to the present invention, the signal measured by the second circuit unit simultaneously contains respiration and body motion information (all of which are signals generated according to vibration and movement of a body surface), and thus a frequency band filter may be separately configured to divide the signal measured by the second circuit unit so as to separate the respiration information and the body motion information from the BCG signal.

In addition, the measuring apparatus according to the present invention may be configured to store the measured ECG, BCG respiration, and human body motion signals in a main processor (MCU) through an ADC and to derive a secondary health index using these information items, to store the measured biomedical signal in a separate storage space such as a micro SD card and EEPROM, or store the biomedical signal in another processing apparatus such as a smart phone, a smart pad, and a computer using wireless communication such as WiFi, Bluetooh, ZigBee, and RF.

FIGS. 9 and 10 are images of an example of a measuring apparatus according to an embodiment of the present invention. FIG. 9 is an image of a state in which an attachment surface of a piezoelectric element 10 is directed upward, and FIG. 10 is an image of a state in which a formation surface of a substrate is directed upward when the measuring apparatus further includes an opposite surface of a piezoelectric element or a substrate.

As described above, the measuring apparatus according to the present invention may further include a separate film type substrate along with a film type piezoelectric element 10. In reality, in the both two cases, the measuring apparatus are configured in the form of a thin film, and thus it is difficult to distinguish the cases with the unaided eye, and as illustrated in FIGS. 9 and 10, in the both two cases, the measuring apparatus according to the present invention is configured in the form of a thin film, and thus it is easy to attach the measuring apparatus onto the skin and a configuration of the measuring apparatus may be very simplified.

Hereinafter, an example of use of a film-type biomedical signal measuring apparatus according to the present invention will be described.

First, a measuring apparatus is attached onto a chest skin surface using an adhesive member.

Then a user lives a daily life while attaching the measuring apparatus for one day and records ECG, BCG, and human body motion materials during the day.

In this case, while the measuring apparatus is attached to the skin and biomedical signal data is measured, the biomedical signal data may wirelessly transmitted to a smart phone, a smart pad, a computer, or the like or may be stored in a storage device in the apparatus, or the transmitting and the storing may be simultaneously performed.

When the biomedical signal data is externally and directly transmitted to a device, the device may process a signal and calculate a target health index, and when the biomedical signal is stored in the storage device, data is measured during about one day, the measuring apparatus is detached from the chest and put on a separate docking system, and then all continuously measured data items may be simultaneously transmitted to a smart phone, a smart pad, a computer, or the like.

In order to extract stored data, the docking system may be configured to transmit the data using near field communication (NFC) or a wireless data transfer protocol (Bluetooth, ZigBee, WiFi, etc.), configured to transmit the data through a contact terminal formed outside the docking system for data transfer, or configured to charge the measuring apparatus.

Then when all the data items measured during one day are extracted and the measuring apparatus is completely charged, the adhesive member is replaced with new one for next day use and data is re-measured.

The film-type biomedical signal measuring apparatus according to the present invention may be configured to simultaneously and simply measure a plurality of biomedical signals such as electrical signals and vibration signals of the human body and to additionally perform signal processing for derivation of health indexes such as a heart rate, a stress index, BCG, blood pressure, the amount of physical activity, a respiration rate, and $VO_2$max using the plurality of biomedical signals.

For example, during the signal processing for derivation of the health indexes, the heart rate may be derived by analyzing an ECG signal, calculating a time interval between R peaks, and then calculating a heart rate per minute. In addition, the stress index may be derived by FFT processing a heart rate to acquire data in a frequency domain, calculating a heart rate ratio between a high frequency region and a high frequency region in the frequency domain.

In addition, the signal measured by the second circuit unit according to the present invention contains all of BCG, respiration, and human body motion information, the BCG signal may be detected from the information by passing the signal measured by the second circuit unit through a band-pass filter of about 0.2 to 10 Hz in order to extract only the BCG signal, the respiration rate may be detected from the signal measured by the second circuit unit through a band-pass filter of about 0.2 to 2 Hz, and the human body motion may be detected through a band-pass filter of about 1 to 30 Hz.

The blood pressure may be estimated by analyzing a time difference between ECG and BCG signals. For example, since an R-peak signal may be generated from the ECG when the heart begins to bit due to electric stimulus and a J peak as a highest peak is generated from the BCG when the heart squirts blood thereafter, a time difference between generation of the R peak from the ECG and generation of the J peak from the BCG may have a direct relation with a systolic blood pressure, and thus a blood pressure may be estimated according to a formula about the formula.

In addition, although the maximal oxygen uptake ($VO_2$max) is a representative index indicating a cardiovascular health degree and is important in that $VO_2$max has an intimate relation with a death rate, since it is cumbersome to measure $VO_2$max, $VO_2$max has not been generally and widely used. However, $VO_2$max may be measured using the measuring apparatus according to the present invention by analyzing an enhancing degree of a heart rate in the case of a specific amount of physical activity and by calculating $VO_2$max using human body motion and the heart rate.

The film-type biomedical signal measuring apparatus according to the present invention may also be configured to determine whether a user is authenticated using a plurality of biomedical signals while simultaneously and simply measuring the biomedical signals such as electrical signals and vibration signals of the human body.

Hereinafter, a blood pressure measuring apparatus for measuring a blood pressure using the aforementioned film-type biomedical signal measuring apparatus will be described in detail with regard to an embodiment of the present invention with reference to the drawing.

FIG. 11 is a schematic diagram illustrating a configuration of a blood pressure measuring apparatus 100 according to an embodiment of the present invention.

The blood pressure measuring apparatus 100 according to the present invention may measure a blood pressure using the aforementioned film-type biomedical signal measuring apparatuses 10 and 40 and each of the film-type biomedical signal measuring apparatuses 10 and 40 may include a film-type piezoelectric element 12, a plurality of metallic thin film electrodes 21, 23, 25, and 31 formed on the piezoelectric element 12, and the first circuit unit 32 and the second circuit unit 33, which measure an ECG signal and a BCG signal from at least two of the plurality of metallic thin film electrodes 21, 23, 25, and 31, respectively. That is, the film-type biomedical signal measuring apparatuses 10 and 40 used in the blood pressure measuring apparatus 100 according to the present invention may be configured in such a way that the first circuit unit 32 measures the ECG signal and the second circuit unit 33 measures the BCG signal. The detailed description of the aforementioned embodiments may be applied in the same way to the detailed description of the film-type biomedical signal measuring apparatuses 10 and 40, and thus the detailed description of the film-type biomedical signal measuring apparatuses 10 and 40 will be omitted here.

Referring to FIG. 11, the film-type blood pressure apparatus 100 according to the present invention may include the film-type biomedical signal measuring apparatuses 10 and 40, and a blood pressure calculator 110 for deriving a blood pressure using the ECG signal and BCG signal measured by the film-type biomedical signal measuring apparatuses 10 and 40.

The blood pressure calculator 110 may measure a blood pressure using a blood pressure estimation regression equation for each user and an R-J time interval between an R-peak value of the ECG signal and a J-peak value of the BCG signal measured by the film-type biomedical signal measuring apparatuses 10 and 40.

The blood pressure calculator 110 may include a detector 112 for detecting an R-peak value from the ECG signal measured by the first circuit unit 32, detecting a J-peak value from the BCG signal measured by the second circuit unit 33, and detecting an R-J time interval between the R-peak value and the J-peak value, and a blood pressure calculator 114 for deriving a blood pressure using the R-J time interval detected by the detector 112.

FIG. 12 is a graph showing a relation between an R-J time interval and a systolic blood pressure (SBP).

As seen from FIG. 12, a time interval between an R-peak value as a peak value in one period of an ECG signal and a J-peak value as a peak value in one period of a BCG signal, that is, the R-J time interval has a relation with the SBP, and thus when the R-J time interval and the SBP are regressed, a blood pressure estimation regression equation may be derived. In addition, a blood pressure may be calculated by inserting the calculated blood pressure estimation regression equation into the R-J time interval value. That is, the blood pressure may be measured by deriving only the R-J time interval from the ECG signal and the BCG signal using the blood pressure estimation regression equation.

The relation between the R-J time interval and the SBP may be different for each respective user, and thus the blood pressure estimation regression equation may also be different for each respective user.

FIGS. 13 to 15 are graphs illustrating a relation between an R-J time interval and a SBP, which is different for each respective user, and as seen from FIGS. 13 to 15, the relation between the R-J time interval and the SBP may be different for each respective user. Accordingly, in order to measure as accurate blood pressure as possible when a blood pressure is measured using the R-J time interval and the blood pressure estimation regression equation, the blood pressure estimation regression equation for each respective user may be used. For example, the blood pressure calculator 114 may calculate a blood pressure using a pre-stored blood pressure estimation regression equation for each user and the R-J time interval, and in this regard, the pre-stored blood pressure estimation regression equation for each user may be a blood pressure estimation regression equation of a subject, which is derived from an R-J time interval and SBP of the subject pre-measured from another measuring apparatus.

The blood pressure measuring apparatus 100 according to the present invention may include at least one of a storage unit 120 for storing the blood pressure calculated by the blood pressure calculator 110 and a display unit 130 for displaying the calculated blood pressure.

Since the blood pressure measuring apparatus 100 according to the present invention may measure a blood pressure using the film-type biomedical signal measuring apparatuses 10 and 40 and may be very thin in the form of a film so as to be easily attached to the skin, it is advantageous to continuously measure the blood pressure without limits of places, and thus when the blood pressure measuring apparatus 100 includes the storage unit 120 that stores the continuously measured blood pressure, detailed biomedical information of a subject may be derived from a blood pressure that is measured continuously or with a time interval. In addition, when the blood pressure measuring apparatus 100 according to the present invention further includes the display unit 130, the blood pressure that is measured continuously or with a time interval may be checked whenever the blood pressure is measured so as to provide blood pressure information to the subject in real time. In addition, when the blood pressure measuring apparatus 100 according to the present invention does not include the display unit 130, the blood pressure measuring apparatus 100 may further include a transmitter (not shown) for transmitting blood pressure data stored in the storage unit 120 to another device that is capable of displaying the data and may further include a power source unit (not shown) for supplying power to the film-type biomedical signal measuring apparatuses 10 and 40.

FIG. 16 is a schematic diagram illustrating a blood pressure measuring apparatus 150 according to an embodiment of the present invention.

Referring to FIG. 16, the blood pressure measuring apparatus 150 according to the present embodiment may be configured in such a way that the film-type biomedical signal measuring apparatuses 10 and 40 and the blood pressure calculator 110 are separately provided. For example, the blood pressure calculator 110 may not be installed in the film-type biomedical signal measuring apparatuses 10 and 40 and may be installed in another device, for example, a separate portable device or a portable smart phone that the subject carries. Accordingly, it may be advantageous that the film-type biomedical signal measuring apparatuses 10 and 40 does not necessarily include the storage unit 120 for storing the blood pressure calculated by the blood pressure calculator 110 and the display unit 130 for displaying the calculated blood pressure.

The blood pressure measuring apparatus 100 according to the present invention may measure a blood pressure using the film-type biomedical signal measuring apparatuses 10 and 40 and may be very thin in the form of a film so as to be easily attached to the skin. As described above, when the blood pressure calculator 110 is included in a separate device other than the film-type biomedical signal measuring apparatuses 10 and 40, the thickness of each of the film-type biomedical signal measuring apparatuses 10 and 40 may become thin so as to be easily attached to the skin.

In this case, the film-type biomedical signal measuring apparatuses 10 and 40 may further include a transmitter 140 that transmits the ECG signal and the BCG signal which are measured by the first circuit unit 32 and the second circuit unit 33, respectively to the blood pressure calculator 110, and the blood pressure calculator 110 may be configured to calculate a blood pressure using the ECG signal and the BCG signal transmitted from the transmitter 140. The transmitter 140 may be configured by wire, wirelessly, or wired/wireless.

In the aforementioned embodiments, the BCG signal may be measured through the piezoelectric elements 12 and 42 according to the second circuit unit 33, but the present invention is not limited thereto, and the blood pressure measuring apparatus according to the present invention may be configured to measure the BCG signal using an acceleration sensor. In general, the BCG signal may be measured by positioning an acceleration sensor on a skin surface and measuring a reaction of a human body according to action of blood.

FIG. 17 is a schematic diagram illustrating a configuration of a blood pressure measuring apparatus 170 for measuring a BCG signal using an acceleration sensor according to an embodiment of the present invention.

Referring to FIG. 17, the blood pressure measuring apparatus 170 according to the present embodiment may include a biomedical signal measuring apparatus 180 including a film-type substrate 181, at least two metallic thin film electrodes 182 that are formed on an attachment surface of the substrate 181 not to be electrically connected to each other, a first circuit unit 183 that is formed on an opposite surface of the substrate 181 so as to measure an ECG signal from the at least two metallic thin film electrodes 182, and a BCG signal measurer 184 for measuring the BCG signal using the acceleration sensor formed on the opposite surface of the substrate 181, and a blood pressure calculator 110 for calculating a blood pressure using the ECG signal and the BCG signal that are measured by the first circuit unit 183 and the BCG signal measurer 184, respectively.

As described above, the blood pressure measuring apparatus 170 according to the present embodiment is different from the aforementioned embodiments except that the BCG signal is measured using an acceleration sensor instead of the piezoelectric elements 12 and 42, and thus the detailed description in the aforementioned embodiments is applied to a detailed description of the other components of the present embodiment.

As described above, the blood pressure measuring apparatus 170 according to the present embodiment may be configured in such a way that an acceleration sensor is formed on the opposite surface of the substrate 181 or a plurality of acceleration sensors are disposed at a separate position from the biomedical signal measuring apparatus 180, but the present invention is not limited thereto.

Hereinafter, a method for measuring a blood pressure using the film-type biomedical signal measuring apparatuses 10, 40, and 180 according to the present invention will be described with regard to an embodiment of the present invention.

As described above, when a blood pressure is measured using the film-type biomedical signal measuring apparatuses 10, 40, and 180 according to the present invention, it is easy to attach the film-type biomedical signal measuring apparatuses 10, 40, and 180 to the skin in the form of a film and an ECG signal and a BCG signal may be simultaneously and continuously measured without limits of places, and thus a blood pressure of a subject may be easily measured in real time without limits of places. For example, when the film-type biomedical signal measuring apparatuses 10, 40, and 180 according to the present invention is configured in such a way that the first circuit unit 32 and the second circuit unit 33 measure an ECG signal and a BCG signal continuously or at a time interval, respectively while being attached to the skin of the subject, the detector 112 continuously derives an R-J time interval from the ECG and the BCG signal that are measured continuously or at a time interval, and the blood pressure calculator 114 calculates a blood pressure using the derived R-J time interval and a blood pressure estimation regression equation for each user, it may be possible to measure a blood pressure of a subject in real time continuously or at a predetermined time interval without limits of places.

A method for measuring a blood pressure according to an embodiment of the present invention may include deriving an R-peak value and a J-peak value from the simultaneously measured ECG signal and BCG signal, respectively, deriving an R-J time interval of the derived R-peak value and J-peak value, and calculating a blood pressure using the derived R-J time interval and a pre-stored blood pressure estimation linear regression equation for each user. Here, the pre-stored blood pressure estimation linear regression equation for each user may be a blood pressure estimation regression equation of a subject, which is pre-derived and stored in the blood pressure measuring apparatuses 100, 150, and 170.

Hereinafter, a cardiopulmonary fitness estimating apparatus for estimating a cardiopulmonary fitness (CPF) index using the aforementioned film-type biomedical signal measuring apparatus will be described in detail with regard to an embodiment of the present invention with reference to the drawing.

FIG. 18 is a schematic diagram illustrating a cardiopulmonary fitness estimating apparatus 200 according to an embodiment of the present invention.

The cardiopulmonary fitness estimating apparatus 200 according to the present invention may measure cardiopulmonary fitness using the aforementioned film-type biomedical signal measuring apparatuses 10 and 40 and may include the film-type biomedical signal measuring apparatuses 10 and 40, and a cardiopulmonary fitness index estimator 210 for estimating a cardiopulmonary fitness index using the ECG signal and the vibration signal measured by the measuring apparatuses 10 and 40. Accordingly, the cardiopulmonary fitness estimating apparatus 200 according to the present invention uses the film-type biomedical signal measuring apparatuses 10 and 40 that may be easily attached to the skin and may simultaneously and continuously measure the ECG signal and the vibration signal and thus may very simply measure cardiopulmonary fitness during a daily life.

The film-type biomedical signal measuring apparatuses 10 and 40 may include the film-type piezoelectric elements 12 and 42, a plurality of metallic thin film electrodes 21, 23, 25, 31, and 34 formed on the piezoelectric elements 12 and 42, and the first circuit unit 32 and the second circuit unit 33 which measure the ECG signal and the vibration signal from at least two of the plurality of metallic thin film electrodes 21, 23, 25, 31, and 34, respectively. That is, the film-type biomedical signal measuring apparatuses 10 and 40 used in the cardiopulmonary fitness estimating apparatus 200 according to the present invention may be configured in such a way that the first circuit unit 32 measures the ECG signal and the second circuit unit 33 measures the vibration signal. The first circuit unit 32 may be an ECG signal processor and may include an instrumentation amp unit and a filter unit, and the biomedical signal the measuring apparatuses 10 and 40 may further include a capacitance preamplifier when being attached to the skin using hydro gel. The second circuit unit 33 may be a vibration signal processor and may include a current-voltage converter and a filter unit, the current-voltage converter may convert current generated by the piezoelectric element 12 into a voltage, and the filter unit may detect an appropriate human body motion signal band from the measured vibration signal. For example, the human body motion signal may be detected by passing a signal measured by the second circuit unit 33 through a band-pass filter of about 1 to 30 Hz. The detailed description of the aforementioned embodiments may be applied in the same way to the detailed description of the film-type biomedical signal measuring apparatuses 10 and 40, and thus the detailed description of the film-type biomedical signal measuring apparatuses 10 and 40 will be omitted here.

The cardiopulmonary fitness index estimator 210 may be configured to measure cardiopulmonary fitness using the ECG signal and the vibration signal measured by the film-type biomedical signal measuring apparatuses 10 and 40 and for example, may be configured to measure maximal oxygen uptake ($VO_2$max) indicating a reaction degree of a human body when load is applied to the human body.

In detail, the cardiopulmonary fitness index estimator 210 may calculate a heart rate at each unit time from the ECG signal that is continuously measured by the first circuit unit 32 for a predetermined measurement time period (e.g., during a daily life), calculate a amount of physical activity at each unit time from the vibration signal that is continuously measured by the second circuit unit 33, extract the heart rate and amount of physical activity data in a period in which the heart rate increases from the calculated heart rate and amount of physical activity data, detect a linear regression equation between the heart rate and the amount of physical activity in the period in which the heart rate increases using the extracted heart rate and amount of physical activity data, calculate maximum activity energy expenditure using the detected linear regression equation, and calculate maximal oxygen uptake ($VO_2$max) using the calculated maximum activity energy expenditure and a pre-stored maximal oxygen uptake estimation equation.

To this end, the cardiopulmonary fitness index estimator 210 may include a first storage unit for storing an ECG signal and a vibration signal that are continuously measured by the first circuit unit 32 and the second circuit unit 33 during a measurement period, respectively, a heart rate calculator for calculating a heart rate (beat/min) at each unit time (e.g., every 1 minute) from the ECG signal stored in the first storage unit, an amount of physical activity calculator for calculating an amount of physical activity (J/min) at each unit time (e.g., every 1 minute) from the vibration stored in the storage unit, a second storage unit for storing the calculated heart rate and amount of physical activity, an extractor for extracting heart rate and amount of physical activity data in a period in which the heart rate increases from the heart rate and amount of physical activity data stored in the second storage unit, a detector for detecting a linear regression equation between the heart rate and the amount of physical activity in the period in which the heart rate increases using the extracted heart rate and amount of physical activity data, a maximum amount of physical activity calculator for calculating maximum activity energy expenditure using the detected linear regression equation, and a maximal oxygen uptake calculator for calculating maximal oxygen uptake using the maximum activity energy expenditure and a pre-stored maximal oxygen uptake estimation regression equation.

Here, only the heart rate and amount of physical activity data in the period in which the heart rate increases is extracted to derive a linear regression equation because a general method for measuring maximal oxygen uptake is performed by monitoring and analyzing a situation in which a human body reacts (heart rate increases) in the human body moves, and thus when only the period in which the heart rate increases is extracted during a daily life, the same effect may be expected as in the general method for measuring maximal oxygen uptake.

FIG. 19 is a graph illustrating heart rate (HR (BPM), beat/min) and an amount of physical activity (activity energy expenditure (aEE)(J/min)) that are calculated and stored every one minute from continuously measured ECG signals and vibration signals, and FIG. 20 is a graph illustrating detection of a linear regression equation by extracting only heart rate and amount of physical activity data in a period (a shaded portion of FIG. 19) in which a heart rate increases.

As shown in FIGS. 19 and 20, when a regression equation is detected by extracting only heart rate and amount of physical activity data in a period in which a heart rate increases from the heart rate and amount of physical activity data calculated every one minute from continuously measured ECG signals and vibration signals, a linear regression equation may be detected as shown in FIG. 2.

In addition, when a maximum heart rate (in general, a maximum heart rate is (220-age)) according to age of a subject is inserted into the detected linear regression equation, maximum activity energy expenditure of the subject may be calculated, and the calculated maximum activity energy expenditure is inserted into a preset maximal oxygen uptake estimation regression equation ($VO_2$max estimation equation) obtained via clinical trial, the maximal oxygen uptake (VO2max) of the subject may be measured.

Compared to measurement of maximal oxygen uptake, the cardiopulmonary fitness index estimator 210 may be configured to measure homeostasis for determining a human body's degree of returning to an original state after load applied to a human body is removed. To this end, compared to measurement of maximal oxygen uptake, the cardiopulmonary fitness index estimator 210 may be configured to extract the heart rate and amount of physical activity data in a period in which the heart rate decreases from the calculated heart rate and amount of physical activity data and to detect a linear regression equation between a heart rate and an amount of physical activity in a period in which the heart rate decreases using the extracted heart rate and amount of physical activity data. Likewise, when the regression equation between the heart rate and the amount of physical activity in the period in which the heart rate decreases is detected, homeostasis as a human body's degree of returning to an original state after load applied to a human body is removed may be measured. Here, the homeostasis may be represented by inclination of the linear regression equation, time taken to return to an original state, or the like.

The cardiopulmonary fitness estimating apparatus 200 according to the present invention may further include a display unit 230 for displaying the cardiopulmonary fitness (e.g., maximal oxygen uptake) calculated by the cardiopulmonary fitness index estimator 210, and a power supply unit (not shown) for supplying power.

As described above, the cardiopulmonary fitness estimating apparatus 200 according to the present invention is a system for estimating a cardiopulmonary fitness index using the film-type biomedical signal measuring apparatuses 10 and 40 and may be very thin in the form of a film so as to be easily attached to the skin, and thus the cardiopulmonary fitness estimating apparatus 200 may continuously measure a ECG signal and a vibration signal without limits of places while being attached to the skin, and when the ECG signal and the vibration that are continuously measured while the cardiopulmonary fitness estimating apparatus 200 is attached to the skin are used, cardiopulmonary fitness such as maximal oxygen uptake may be easily and simply measured during a daily life. Accordingly, personal physical health as well as personal physic al activity may be managed by continuous measuring and managing cardiopulmonary fitness to highly help personal health maintenance, and cardiopulmonary fitness is not necessarily measured through intended sub-maximal exercise, and thus cardiopulmonary fitness of patients and elderly people as well as healthy people may also be easily and safely measured.

FIG. 21 is a schematic diagram illustrating a configuration of a cardiopulmonary fitness measuring system according to another embodiment of the present invention.

Referring to FIG. 21, a cardiopulmonary fitness estimating apparatus 250 according to the present embodiment may be configured in such a way that the film-type biomedical signal measuring apparatuses 10 and 40 and the cardiopulmonary fitness index estimator 210 are separately installed. For example, the cardiopulmonary fitness index estimator 210 may be installed in another device, for example, a separate portable device or a smart phone that a subject carries rather than being installed in the film-type biomedical signal measuring apparatuses 10 and 40.

The cardiopulmonary fitness estimating apparatus according to the present invention may estimate cardiopulmonary fitness using the film-type biomedical signal measuring apparatuses 10 and 40 and may be very thin in the form of a film so as to be easily attached to the skin. As described above, when the cardiopulmonary fitness index estimator 210 is installed in a separate device other than the film-type biomedical signal measuring apparatuses 10 and 40, the film-type biomedical signal measuring apparatuses 10 and 40 may be further thinned accordingly so as to be more easily attached onto the skin.

In this case, the film-type biomedical signal measuring apparatuses 10 and 40 may further include a transmitter 240 for transmitting the ECG signal and the vibration signal that are measured by the first circuit unit 32 and the second circuit unit 33, respectively to the cardiopulmonary fitness index estimator 210, and the cardiopulmonary fitness index estimator 210 may be configured to measure cardiopulmonary fitness using the ECG signal and the vibration signal transmitted from the transmitter 240. The transmitter 240 may be configured by wire, wirelessly, or wired/wireless.

In the aforementioned embodiments, the human body motion signal for estimation of the amount of physical activity is measured by measuring the vibration signal of the piezoelectric elements 12 and 42 according to the second circuit unit 33, but the present invention is not limited thereto, and the cardiopulmonary fitness estimating apparatus according to the present invention may be configured to measure a human body motion signal using an acceleration sensor or may further include an acceleration sensor, which will be described in detail with reference to the drawing.

FIG. 22 is a schematic diagram illustrating a configuration of a cardiopulmonary fitness estimating apparatus for measuring a human body motion signal using only an acceleration sensor without using a vibration signal of a piezoelectric element, according to an embodiment of the present invention.

Referring to FIG. 22, a cardiopulmonary fitness estimating apparatus 270 according to the present embodiment may include a biomedical signal measuring apparatus 280 including a film-type substrate 281, at least two metallic thin film electrodes 282 that are formed on an attachment surface of the substrate 281 not to be electrically connected to each other, a first circuit unit 283 that is formed on an opposite surface of the substrate 281 so as to measure an ECG signal from the at least two metallic thin film electrodes 282, and an acceleration sensor 284 formed on the opposite surface of the substrate 281, and the cardiopulmonary fitness index estimator 210 for calculating a heart rate from the ECG signal measured by the first circuit unit 283, calculating an amount of physical activity from the human body motion signal measured by the acceleration sensor 284, and measuring cardiopulmonary fitness using the calculated heart rate and amount of physical activity.

As described above, the cardiopulmonary fitness estimating apparatus 270 according to the present embodiment is different from the aforementioned embodiment in that a human body motion signal is measured by the acceleration sensor 284 instead of use of the vibration signal of the piezoelectric elements 12 and 42, and thus the detailed description of the aforementioned embodiments is applied in the same way to other components of the present embodiment.

As described above, the cardiopulmonary fitness estimating apparatus 270 according to the present embodiment may be configured in such a way that the acceleration sensor 284 may be formed on the opposite surface of the substrate 281 or configured in such a way that a plurality of acceleration sensors may be formed at a separate position from the biomedical signal measuring apparatus 280, but the present invention is not limited thereto.

FIG. 23 is a schematic diagram illustrating a cardiopulmonary fitness measuring system that uses a vibration signal of a piezoelectric element and further includes an acceleration sensor, according to an embodiment of the present invention.

Referring to FIG. 23, a cardiopulmonary fitness estimating apparatus 290 according to the present embodiment may further include an acceleration sensor 284 for measuring a human body motion signal in addition to the biomedical signal the measuring apparatuses 10 and 40. The acceleration sensor 284 may be installed directly in biomedical signal the measuring apparatuses 10 and 40 or a plurality of acceleration sensors may be installed in a specific part such as an arm and a leg separately from the biomedical signal the measuring apparatuses 10 and 40. In this case, the cardiopulmonary fitness index estimator 210 may multiply use the human body motion signal measured by the acceleration sensor 284 along with the vibration signal measured by the second circuit unit 33 to calculate an amount of physical activity.

Since the acceleration sensor 284 directly measures acceleration according to human body motion, the acceleration sensor 284 may easily measure the human body motion signal, but when a subject is moved by external force such as in an automobile and an elevator, an issue also occurs in that movement according to the external force is measured as if the subject moves. On the other hand, since the vibration signal of the piezoelectric elements 12 and 42 is measured by the second circuit unit 33 of the film-type biomedical signal measuring apparatuses 10 and 40 while the film-type biomedical signal measuring apparatuses 10 and 40 is attached directly to the skin of the human body, there is no need to worry about measuring movement according to external force of the subject as movement according to motion of the subjection. Accordingly, like in the present embodiment, when a human body motion signal for calculation of the amount of physical activity is multiply used together with the signal measured by the acceleration sensor 284 and the vibration signal measured by the second circuit unit 33, the above issue may be prevented so as to measure an accurate human body motion signal, thereby enhancing accuracy of estimation of the amount of physical activity used to measure cardiopulmonary fitness.

For example, the cardiopulmonary fitness index estimator 210 may be configured to calculate the amount of physical activity using both of the signals measured by the second circuit unit 33 and the acceleration sensor 284 or configured to calculate two amounts of physical activity from the respective signals measured by the second circuit unit 33 and the acceleration sensor 284 and to calculate an average value of the two calculated amount of physical activity as an actual amount of physical activity. The cardiopulmonary fitness index estimator 210 may calculate the amount of physical activity calculated from the signal measured by the acceleration sensor 284 as an actual amount of physical activity and use the vibration single measured by the second circuit unit 33 as data for determining whether the signal measured by the acceleration sensor 284 is a signal that is actually generated according to motion of the subject. For example, the cardiopulmonary fitness index estimator 210 may be configured to calculate the amount of physical activity calculated using the signal measured by the acceleration sensor 284 as an actual amount of physical activity when the amount of physical activity calculated using the signal measured by the acceleration sensor 284 is compared with the amount of physical activity calculated using the signal measured by the second circuit unit 33, if a difference between the two calculated amounts of physical activity is within an error range and to determine that the subject is moved by external force and exclude the measured value or to calculate the amount of physical activity calculated using the vibration signal measured by the second circuit unit 33 as an actual amount of physical activity if the difference between the two calculated amounts of physical activity is very large to be equal to or greater than the error range, thereby preventing measurement error of the acceleration sensor 284, which is generated due to movement according to external force.

According to other embodiments of the present invention, the cardiopulmonary fitness estimating apparatuses 200, 250, 270, and 290 may be configured in such a way that the film-type biomedical signal measuring apparatuses 10, 40, and 280 directly calculate a heart rate and an amount of physical activity. To this end, the first circuit unit 32 may be configured to calculate a hear rate from the continuously measured ECG signal at each unit time and the second circuit unit 33 may be configured to calculate an amount of physical activity from the continuously measured vibration signal at each unit time. In this case, the cardiopulmonary fitness index estimator 210 may estimate a cardiopulmonary fitness index using the heart rate that is calculated by the first circuit unit 32 at each unit time and the amount of physical activity that is calculated by the second circuit unit 33 at each unit time. The heart rate may be calculated by circuit-configuring the first circuit unit 32 to calculate the number of peak points (R peaks) at each unit time from the continuously measured ECG signal and the amount of physical activity may be calculated by circuit-configuring the second circuit unit 33 to calculate the amount of physical activity from the continuously measured vibration signal.

Hereinafter, a method for estimating cardiopulmonary fitness using the film-type biomedical signal measuring apparatuses 10 and 40 will be described in detail with regard to an embodiment of the present invention.

As described above, since the film-type biomedical signal measuring apparatuses 10, 40, and 280 according to the present invention may be easily attached to the skin in the form of a film by estimating cardiopulmonary fitness, the ECG signal and the human body motion signal may be continuously and simultaneously measured without limits of places, and accordingly the cardiopulmonary fitness of the subject may be easily estimated without limits of places during a daily life.

First, in the method for estimating cardiopulmonary fitness according to the present invention, a subject lives a daily life while the film-type biomedical signal measuring apparatuses 10 and 40 is attached onto the skin for a predetermined measurement period.

In this case, the ECG signal and the human body motion signal are simultaneously and continuously measured and stored during a daily life. Here, the human body motion signal may be a vibration signal measured by the second circuit unit 33, a signal measured by the acceleration sensor 284, or all signals measured by the second circuit unit 33 and the acceleration sensor 284, but the present invention is not limited thereto.

Then a heart rate (beat/min) is calculated from the stored ECG signal and stored every one minute, and an amount of physical activity (J/min) is calculated from the stored human body motion signal and stored every one minute. Here, the heart rate may be calculated by analyzing the ECG signal and calculating a time interval between R peaks to calculate a beat per minute or to calculate the number of R peaks per minute. The amount of physical activity may be calculated using the human body motion signal and a weight of the subject.

Then only heart rate and amount of physical activity data in a period in which the heart rate continuously increases (e.g., the heart rate increases for minimum of 2 minutes) is extracted from the heart rate and amount of physical activity data that is calculated and stored for the measurement time.

Then a linear regression equation between the heart rate and the amount of physical activity in a period in which the heart rate increases is detected using the extracted heart rate and amount of physical activity data.

Then estimated maximum activity energy expenditure of the subject is calculated using a maximum heart rate (which may be generally calculated according to Expression (220−age)) based on an age for each user according to the detected linear regression equation.

Then maximal oxygen uptake of the subject may be calculated according to a relation equation (a maximal oxygen uptake estimation regression equation) established from prior research using the calculated maximum activity energy expenditure and body size.

An example of the maximal oxygen uptake estimation regression equation is as follows.

$$VO_2max=0.103*aEEmax-31.952*height+92.532$$

Here, $VO_2max$ is maximal oxygen uptake, aEEmax is maximum activity energy expenditure, height is the height of the subject, and coefficients and human size parameters in the equation may be changed.

In the method for estimating cardiopulmonary fitness according to the present invention, homeostasis for determining a human body's degree of returning to an original state after load applied to a human body is removed may also be measured by extracting only heart rate and amount of physical activity data in a period in which the heart rate increases from the heart rate and the amount of physical activity that are stored for the measurement period and detecting a linear regression equation between the extracted heart rate and amount of physical activity. Here, the homeostasis may be represented by inclination of the linear regression equation, time taken to return to an original state, or the like.

Here, a personal authentication apparatus for determining whether a user is authenticated using the aforementioned film-type biomedical signal measuring apparatus will be described in detail with regard to an embodiment of the present invention with reference to the drawing.

FIG. 24 is a schematic diagram illustrating a configuration of a personal authentication apparatus 300 according to an embodiment of the present invention.

The personal authentication apparatus 300 according to the present invention may determine whether a user is authenticated using the aforementioned film-type biomedical signal measuring apparatuses 10 and 40, and the film-type biomedical signal measuring apparatuses 10 and 40 may include a film-type piezoelectric element 12, the plurality of metallic thin film electrodes 21, 23, 25, and 31 formed on the piezoelectric element 12, and the first circuit unit 32 and the second circuit unit 33 that measure an ECG signal and a BCG signal from at least two of the plurality of metallic thin film electrodes 21, 23, 25, and 31, respectively. That is, the film-type biomedical signal measuring apparatuses 10 and 40 used in the personal authentication apparatus 300 according to the present invention may be configured in such a way that the first circuit unit 32 measures the ECG signal and the second circuit unit 33 measures the BCG signal. The detailed description of the aforementioned embodiments may be applied in the same way to the detailed description of the film-type biomedical signal measuring apparatuses 10 and 40, and thus the detailed description of the film-type biomedical signal measuring apparatuses 10 and 40 will be omitted here.

Referring to FIG. 24, the personal authentication apparatus 300 according to an embodiment of the present invention may include the film-type biomedical signal measuring apparatuses 10 and 40, and a personal authentication unit 310 for determining whether a user is authenticated using the ECG signal and the BCG signal that are measured from the film-type biomedical signal measuring apparatuses 10 and 40.

The personal authentication unit 310 may determine whether the user is authenticated by comparing an ECG fiducial value and BCG fiducial value of an authentication target, which are detected from the ECG signal and the BCG signal measured from the film-type biomedical signal measuring apparatuses 10 and 40, with a pre-stored ECG fiducial value and BCG fiducial value of a registration target, respectively.

To this end, the personal authentication unit 310 may include a database (DB) 312 for storing the ECG fiducial value and BCG fiducial value of the registration target, a detector for detecting an ECG fiducial value from the ECG signal of the authentication target measured by the first circuit unit 32 and detecting the BCG fiducial value from the BCG signal of the authentication target measured by the second circuit unit 33, and an authentication processor 315 for comparing the ECG fiducial value and BCG fiducial value of the authentication target detected by the detector 314 with the ECG fiducial value and BCG fiducial value of the registration target stored in the DB 312, respectively to determine whether the user is authenticated.

Likewise, since the personal authentication apparatus 300 according to the present invention determine whether the user is authenticated by multiply using the ECG signal and the BCG signal, the accuracy of personal authentication may be enhanced accordingly.

Here, determination of whether a user is authenticated may be interpreted as determining whether the authentication target corresponds to the registration target, and the ECG fiducial value and the BCG fiducial value may refer to reference values for determination of whether the user is authenticated.

FIG. 25 is a graph illustrating an example of ECG fiducial values detected from an ECG signal, and FIG. 26 is a graph illustrating an example of BCG fiducial values detected from a BCG signal.

As seen from FIG. 25, it is well known that a plurality of fiducial points L', P, P', Q, R, S, S', T, T', etc. are present in an ECG signal waveform and that personal authentication is performed through a specific combination of a relative interval or a magnitude ratio between the plurality of fiducial points, a frequency component, and so on.

Accordingly, like values represented by a plurality of numbers of FIG. 25, an ECG fiducial value as a reference value for determination of personal authentication may include any one or a combination of two selected from the group consisting of a relative interval or magnitude ratio, or the like between a plurality of fiducial values.

As shown in FIG. 26, a plurality of fiducial points H, I, J, K, L, M, N, O, etc. are present in the BCG signal waveform like in the ECG signal waveform, and accordingly a BCG fiducial value as a reference for determination of personal authentication may include any one or a combination of two selected from the group consisting of a relative interval or magnitude ratio, or the like between a plurality of fiducial values, such as values in F1 to F12 indicated in FIG. 13.

Since the personal authentication apparatus 300 according to the present invention determines whether the user is authenticated using the film-type biomedical signal measuring apparatuses 10 and 40 that is formed in the form of a film so as to be easily attached to the skin, whether the user is authenticated may be determined while the personal authentication apparatus 300 is attached to the skin during a daily life so as to continuously determine whether the user is authenticated without limits of places.

In this case, the ECG fiducial value and BCG fiducial value of the registration target stored in the DB 312 may be detected from the ECG signal and BCG signal, respectively that are initially measured after the biomedical signal the measuring apparatuses 10 and 40 are attached to the skin of the registration target, and the ECG fiducial value and BCG fiducial value of the authentication target detected by the detector 314 may be detected from the ECG signal and the BCG signal of the registration target, respectively that are measured by the biomedical signal the measuring apparatuses 10 and 40 attached to the skin of the registration target at a specific time for personal authentication.

Accordingly, the personal authentication apparatus 300 according to the present invention may be used as a personal authentication sensor based on a biomedical signal, which may determine whether a user is authenticated in real time without limits of places while being attached to the skin of the registration target during a daily life.

The personal authentication unit 310 may further include a transmitter 317 for transmitting the personal authentication determining result that is continuously obtained in real time without limits of places to a device or system that requires personal authentication for security, electronic payment, etc. The transmitter 317 may be configured by wire, wirelessly, or wired/wireless.

When the personal authentication apparatus 300 is attached to the skin of the registration target, the biomedical signal the measuring apparatuses 10 and 40 may measures an ECG signal and a BCG signal continuously or at a predetermined time interval, and in this case, the personal authentication unit 310 may further include a DB updating unit (not shown) for detecting the ECG fiducial value and the BCG fiducial value from the ECG signal and the BCG signal that are measured continuously or at a predetermined time interval by the biomedical signal the measuring apparatuses 10 and 40, respectively and storing the ECG fiducial value and the BCG fiducial value in the DB 312.

A biomedical signal of the ECG signal and BCG signal measured by the biomedical signal the measuring apparatuses 10 and 40 may be changed according to change in health of the registration target, and the change in the biomedical signal may cause measurement error. In this regard, when the personal authentication unit 310 further includes the DB update unit, even if a heart rate of the registration target is changed according to change in health to change a heart behavior, the heart rate may be checked continuously or at a predetermined time interval and the ECG fiducial value and the BCG fiducial value may be automatically updated, and thus even if a biomedical signal is changed according to change in a health state or health behavior of the registration target, the DB 312 may be automatically updated according to the change so as to configure the DB 312 optimized to the registration target, thereby remarkably reducing measurement error according to change in the biomedical signal.

FIG. 27 is a schematic diagram illustrating a configuration of a personal authentication apparatus 350 according to another embodiment of the present invention.

Referring to FIG. 27, the personal authentication apparatus 350 according to the present embodiment may be configured in such a way that the film-type biomedical signal measuring apparatuses 10 and 40 and the personal authentication unit 310 are separately installed. For example, the personal authentication unit 310 may be installed in another device, for example, a separate portable device or a smart phone that a subject carries rather than being installed in the film-type biomedical signal measuring apparatuses 10 and 40.

The personal authentication unit according to the present invention may determine whether a user is authenticated using the film-type biomedical signal measuring apparatuses 10 and 40 and may be very thin in the form of a film so as to be easily attached to the skin. As described above, when the personal authentication unit 310 is installed in a separate device other than the film-type biomedical signal measuring apparatuses 10 and 40, the film-type biomedical signal measuring apparatuses 10 and 40 may be further thinned accordingly so as to be more easily attached onto the skin.

In this case, the film-type biomedical signal measuring apparatuses 10 and 40 may further include a transmitter 340 for transmitting the ECG signal and the vibration signal that are measured by the first circuit unit 32 and the second circuit unit 33, respectively to the personal authentication unit 310, and the personal authentication unit 310 may be configured to determine whether the user is authenticated using the ECG signal and BCG signal transmitted by the transmitter 340. The transmitter 340 may be configured by wire, wirelessly, or wired/wireless.

In the aforementioned embodiments, the BCG signal is measured by the piezoelectric elements 12 and 42 according to the second circuit unit 33, but the present invention is not limited thereto, and the personal authentication apparatus according to the present invention may be configured to measure a BCG signal using an acceleration sensor. In general, the BCG signal may be measured by positioning the acceleration sensor on a skin surface and then measuring a reaction of the human body according to blood action.

FIG. 28 is a schematic diagram illustrating a personal authentication apparatus 370 for measuring a BCG signal using an acceleration sensor, according to an embodiment of the present invention.

Referring to FIG. 28, the personal authentication apparatus 370 according to the present embodiment may include a biomedical signal measuring apparatus 380 including a film-type substrate 381, at least two metallic thin film electrodes 382 that are formed on an attachment surface of the substrate 381 not to be electrically connected to each other, a first circuit unit 383 that is formed on an opposite surface of the substrate 381 so as to measure an ECG signal from the at least two metallic thin film electrodes 382, and a BCG signal measurer 384 for measuring the BCG signal using an acceleration sensor formed on the opposite surface of the substrate 381, and the personal authentication unit 310 for determining whether a user is authenticated using the ECG signal and the BCG signal that are measured by the first circuit unit 383 and BCG signal measurer 384, respectively.

As described above, the personal authentication apparatus 370 according to the present embodiment is different from in the aforementioned embodiments except that a BCG signal is measured using the acceleration sensor instead of the piezoelectric elements 12 and 42, and accordingly the detailed description of the aforementioned embodiments is applied in the same way to other components of the present embodiment.

As described above, the personal authentication apparatus 370 according to the present embodiment may be configured in such a way that the acceleration sensor may be formed on the opposite surface of the substrate 381 or configured in such a way that a plurality of acceleration sensors may be formed at a separate position from the biomedical signal measuring apparatus 380, but the present invention is not limited thereto.

Hereinafter, a personal authentication method using the film-type biomedical signal measuring apparatuses 10 and 40 according to the present invention will be described in detail with regard to an embodiment of the present invention.

First, the personal authentication method according to an embodiment of the present invention may include detecting a ECG fiducial value and BCG fiducial value of an authentication target from simultaneously measured ECG signal and BCG signal, respectively, and determining whether a user is authenticated by comparing the detected ECG fiducial value and BCG fiducial value of the authentication target with pre-stored ECG fiducial value and BCG fiducial value of the registration target, respectively.

As described above, when whether a user is authenticated is determined using the film-type biomedical signal measuring apparatuses 10, 40, and 380 according to the present invention, since the film-type biomedical signal measuring apparatuses 10, 40, and 380 is easily attached to the skin in the form of a film, an ECG signal and a BCG signal may be continuously and simultaneously measured without limits of places while being attached to the skin of the registration target, and thus the personal authentication apparatuses 300, 350, and 370 according to the present invention may be used as a biomedical signal-based personal authentication sensor for determining whether the registration target is authenticated in real time during a daily life without limits of places.

A personal authentication method using a biomedical signal-based personal authentication sensor according to an embodiment of the present invention may include attaching the film-type biomedical signal measuring apparatuses 10, 40, and 380 to the skin of a registration target, detecting an ECG fiducial value and a BCG fiducial value from an ECG signal and a BCG signal, respectively that are initially and simultaneously measured by the film-type biomedical signal measuring apparatuses 10, 40, and 380 and storing the ECG fiducial value and the BCG fiducial value of the registration target in the DB 312, detecting an ECG fiducial value and a BCG fiducial value from an ECG signal and a BCG signal, respectively that are thereafter and simultaneously measured by the film-type biomedical signal measuring apparatuses 10, 40, and 380 at a specific time point for personal authentication, and comparing the detected ECG fiducial value and BCG fiducial value with the ECG fiducial value and the BCG fiducial value of the registration target, respectively to determine whether the registration target is authenticated.

The method may further include detecting an ECG fiducial value and a BCG fiducial value from an ECG signal and a BCG signal, respectively that are continuously or a predetermined time interval by the film-type biomedical signal measuring apparatuses 10, 40, and 380 attached to the skin of the registration target and storing the ECG fiducial value and the BCG fiducial value in the DB 312.

As described above, the present invention relates to a film-type biomedical signal measuring apparatus configured in such a way that a plurality of metallic thin film electrodes and a circuit unit are formed on a piezoelectric element in the form of a film so as to be easily attached to the skin and a vibration signal and an electrical signal of a human body is simultaneously measured using the plurality of metallic thin film electrodes and the circuit unit, and embodiments of the present invention may be changed in various forms. Accordingly, the present invention is not limited to the embodiments described in the specification, and any form in which ordinary skill in the art can change may be within the scope of the present invention.

What is claimed is:

1. A film-type biomedical signal measuring apparatus comprising:
    a film-type piezoelectric element;
    a plurality of metallic thin film electrodes formed on the piezoelectric element;
    a first circuit unit for measuring a biomedical evoked potential from at least two of the plurality of metallic thin film electrodes; and
    a second circuit unit for measuring a biomedical evoked vibration signal from at least two of the plurality of metallic thin film electrodes,
    wherein the plurality of metallic thin film electrodes comprises two or more first metallic thin film electrodes formed on an attachment surface of the piezoelectric element so as not to be electrically connected to each other, and a second metallic thin film electrode formed on an opposite surface of the piezoelectric element,
    wherein the first circuit unit is formed on the opposite surface of the piezoelectric element so as to be electrically connected to at least two first metallic thin film electrode among the first metallic thin film electrodes, and
    wherein the second circuit unit is formed on the opposite surface of the piezoelectric element so as to be electrically connected to at least one first metallic thin film electrode among the first metallic thin film electrodes and the second metallic thin film electrode.

2. The film-type biomedical signal measuring apparatus of claim 1, wherein
    the first circuit unit measures an ECG signal from the measured biomedical evoked potential, and
    the second circuit unit measures a ballistocardiogram (BCG) signal from the measured biomedical evoked vibration signal.

3. A film-type biomedical signal measuring apparatus comprising:
    a film-type piezoelectric element;
    a plurality of metallic thin film electrodes formed on the piezoelectric element;
    a first circuit unit for measuring a biomedical evoked potential from at least two of the plurality of metallic thin film electrodes; and
    a second circuit unit for measuring a biomedical evoked vibration signal from at least two of the plurality of metallic thin film electrodes,
    wherein the plurality of metallic thin film electrodes comprises at least two first metallic thin film electrode formed on an attachment surface of the piezoelectric element so as not to be electrically connected to each other, and a second metallic thin film electrode formed on an opposite surface of the piezoelectric element,
    wherein the film-type biomedical signal measuring apparatus further comprises a film-type substrate with an adhesion surface adhered to the opposite surface of the piezoelectric element,
    wherein a third metallic thin film electrode electrically connected to at least one first metallic thin film electrode among the first metallic thin film electrodes is formed on a formation surface of the film-type substrate,
    wherein the first circuit unit is formed on the formation surface of the film-type substrate so as to be electrically connected to at least two first metallic thin film electrodes among the first metallic thin film electrodes, and
    wherein the second circuit unit is formed on the formation surface of the film-type substrate so as to be electrically connected to the second metallic thin film electrode and the third metallic thin film electrode.

4. The film-type biomedical signal measuring apparatus of claim 3, wherein the first circuit unit is electrically connected to the third metallic thin film electrode and measures a potential difference between the remaining first metallic thin film electrodes using the any one first metallic thin film electrode as a reference electrode to measure an electrocardiogram (ECG) signal.

5. The film-type biomedical signal measuring apparatus of claim 3, further comprising an adhesive member disposed on any one of surfaces of the piezoelectric element or disposed to surround the piezoelectric element and the film-type substrate to allow any one of the piezoelectric element to be easily attached to a skin.

6. The film-type biomedical signal measuring apparatus of claim 3, wherein
    the first circuit unit measures an ECG signal from the measured biomedical evoked potential, and
    the second circuit unit measures a ballistocardiogram (BCG) signal from the measured biomedical evoked vibration signal.

7. A film-type biomedical signal measuring apparatus comprising:
    a film-type piezoelectric element;
    a plurality of metallic thin film electrodes formed on the piezoelectric element;
    a first circuit unit for measuring a biomedical evoked potential from at least two of the plurality of metallic thin film electrodes; and
    a second circuit unit for measuring a biomedical evoked vibration signal from at least two of the plurality of metallic thin film electrodes,
    wherein the plurality of metallic thin film electrodes comprise at least two first metallic thin film electrodes formed on an attachment surface of the piezoelectric element so as not to be electrically connected to each other, and a second metallic thin film electrode formed on an opposite surface of the piezoelectric element,
    wherein the film-type biomedical signal measuring apparatus further comprises a film-type substrate with an adhesion surface adhered to the opposite surface of the piezoelectric element,
    wherein a third metallic thin film electrode is formed on a formation surface of the film-type substrate so as to be electrically connected to any one of the first metallic thin film electrodes,
    wherein the first circuit unit is formed on the formation surface of the film-type substrate so as to be electrically connected to remaining first metallic thin film electrodes except for the any one first metallic thin film electrode, and
    wherein the second circuit unit is formed on the formation surface of the film-type substrate so as to be electrically connected to the second metallic thin film electrode and the third metallic thin film electrode.

8. The film-type biomedical signal measuring apparatus of claim 7, wherein the first circuit unit is electrically connected to the third metallic thin film electrode and measures a potential difference between the remaining first metallic thin film electrodes using the any one first metallic thin film electrode as a reference electrode to measure an electrocardiogram (ECG) signal.

9. The film-type biomedical signal measuring apparatus of claim 7, further comprising an adhesive member disposed on any one of surfaces of the piezoelectric element or disposed to surround the piezoelectric element and the film-type substrate to allow any one of the piezoelectric element to be easily attached to a skin.

10. The film-type biomedical signal measuring apparatus of claim 7, wherein
the first circuit unit measures an ECG signal from the measured biomedical evoked potential, and
the second circuit unit measures a ballistocardiogram (BCG) signal from the measured biomedical evoked vibration signal.

* * * * *